United States Patent
Thomson et al.

(10) Patent No.: US 11,566,229 B2
(45) Date of Patent: Jan. 31, 2023

(54) EXPANSION AND MAINTENANCE OF ADULT PRIMARY HUMAN HEPATOCYTES IN CULTURE

(71) Applicant: Wisconsin Alumni Research Foundation, Madison, WI (US)

(72) Inventors: James A. Thomson, Madison, WI (US); Srikumar Sengupta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 444 days.

(21) Appl. No.: 16/557,404

(22) Filed: Aug. 30, 2019

(65) Prior Publication Data

US 2020/0071664 A1  Mar. 5, 2020

Related U.S. Application Data

(60) Provisional application No. 62/815,606, filed on Mar. 8, 2019, provisional application No. 62/725,481, filed on Aug. 31, 2018.

(51) Int. Cl.
*C12N 5/071* (2010.01)
*A61K 35/407* (2015.01)

(52) U.S. Cl.
CPC ............ *C12N 5/067* (2013.01); *A61K 35/407* (2013.01); *C12N 2500/30* (2013.01); *C12N 2501/11* (2013.01); *C12N 2501/33* (2013.01); *C12N 2501/39* (2013.01); *C12N 2501/40* (2013.01); *C12N 2502/02* (2013.01)

(58) Field of Classification Search
CPC ................ C12N 5/067; C12N 2501/11; C12N 2501/39; C12N 2501/40; C12N 2502/02
See application file for complete search history.

(56) References Cited

U.S. PATENT DOCUMENTS

2018/0015126 A1  1/2018  Thomson

FOREIGN PATENT DOCUMENTS

WO          98/45479       10/1998
WO       2014124527 A1     8/2014

OTHER PUBLICATIONS

Kim et al., Small molecule-mediated reprogramming of human hepatocytes into bipotent progenitor cells. Journal of Hepatology, vol. 70, No. 1 (Jan. 2019) pp. 97-107. (Year: 2019).*
Sengupta et al., Co-culture with mouse embryonic fibroblasts improves maintenance of metabolic function of human small hepatocyte progenitor cells. Current Research in Toxicology, vol. 1 (Jun. 2020) pp. 70-84. (Year: 2020).*
Avril A, et al. (2004). Mature hepatocytes are the source of small hepatocyte-like progenitor cells in the retrorsine model of liver injury. J Hepatol. 41(5):737-43.
Best DH, et al. (2010). Liver regeneration by small hepatocyte-like progenitor cells after necrotic injury by carbon tetrachloride in retrorsine-exposed rats. Exp Mol Pathol. 89(2): 92-8.
Chen G, et al. (2011). Chemically defined conditions for human iPSC derivation and culture. Nat Methods. 8(5): 424-9.
Gordon GJ, et al. (2002). Isolation, short-term culture, and transplantation of small hepatocyte-like progenitor cells from retrorsine-exposed rats. Transplantation. 73(8): 1236-43.
Hou, Z, et al. "A cost-effective RNA sequencing protocol for large-scale gene expression studies." Scientific reports 5 (2015): 9570.
Katsuda T, et al. (2017). Conversion of Terminally Committed Hepatocytes to Culturable Bipotent Progenitor Cells with Regenerative Capacity. Cell Stem Cell. 20(1): 41-55.
Kibschull, M, et al. "Human embryonic fibroblasts support single cell enzymatic expansion of human embryonic stem cells in xeno-free cultures." Stem cell research 6.1 (2011): 70-82.
Mazza et al. "Decellularized human liver as natural 3D-scaffold for liver bioengineering and transplantation," Sci Rep 2015, 5:13079.
Mitaka T, et al. (1999). Reconstruction of hepatic organoid by rat small hepatocytes and hepatic nonparenchymal cells. Hepatology. 29(1): 111-25.
Ping C, et al. (2006). Hepatic sinusoidal endothelial cells promote hepatocyte proliferation early after partial hepatectomy in rats. Arch Med Res. 37(5): 576-83.
Shan, J., et al. "Identification of small molecules for human hepatocyte expansion and iPS differentiation." Nature chemical biology 9.8 (2013): 514.
Sidler Pfandler, MA, et al. "Small hepatocytes in culture develop polarized transporter expression and differentiation." Journal of cell science 117.18 (2004): 4077-4087.
Zhang, K., et al. "In vitro expansion of primary human hepatocytes with efficient liver repopulation capacity." Cell stem cell 23.6 (2018): 806-819.

* cited by examiner

*Primary Examiner* — Kara D Johnson
(74) *Attorney, Agent, or Firm* — McDonnell Boehnen Hulbert & Berghoff LLP

(57) ABSTRACT

Methods for derivation, culture, and maturation of small hepatic progenitor cells are described.

7 Claims, 18 Drawing Sheets
(13 of 18 Drawing Sheet(s) Filed in Color)

EXPANSION AND MAINTENANCE OF ADULT PRIMARY HUMAN HEPATOCYTES IN CULTURE

CROSS-REFERENCE TO RELATED APPLICATIONS

This application claims priority to U.S. Provisional Patent Application No. 62/725,481 filed Aug. 31, 2018 and U.S. Provisional Patent Application No. 62/815,606 filed Mar. 8, 2019, each of which is incorporated herein by reference in its entirety.

STATEMENT REGARDING FEDERALLY SPONSORED RESEARCH

This invention was made with government support under 83573701 awarded by the Environmental Protection Agency. The government has certain rights in the invention.

BACKGROUND

In vitro model systems employing explanted primary human hepatocytes (PHHs) in culture provide an essential tool for study of liver diseases, hepatotoxicity, hepatotropic viruses, and drug and antiviral development. However, the lack of availability, significant donor-to-donor variability, and rapid de-differentiation of PHHs in culture severely hinders their use in research. PHHs lose their mature phenotype shortly after isolation or removal from their in vivo environment. Efforts to maintain mature PHHs in long-term culture, or to mature fetal hepatic cells in culture, have shown limited success. Sandwich and aggregate culture systems, designed to mimic the in vivo microenvironment of hepatocytes, and methods for co-culturing hepatocytes with non-parenchymal liver cells have not significantly enhanced the viability or maintained the maturity of cultured PHHs and have also failed to mature fetal hepatocytes.

A healthy human liver has an enormous capacity to regenerate. In rodent models, small hepatocyte progenitor cells (SHPCs) rapidly proliferate upon injury to restore liver mass. Rodent small hepatocytes proliferate in culture, but the art has not successfully isolated human small hepatocytes in culture.

Thus, there is a need in the art for methods for growing and expanding human SHPCs in culture.

SUMMARY OF THE INVENTION

In a first aspect, provided herein is a method for obtaining small hepatocyte progenitor cells, the method comprising culturing human hepatocytes in the presence of embryonic fibroblasts in a culture medium that comprises N2 and B27, whereby a cell population comprising $CD44^+$ small hepatocyte progenitor cells is obtained. In some embodiments, the culture medium further comprises dexamethasone and epidermal growth factor. In some embodiments, the human hepatocytes are selected from the group consisting of primary human hepatocytes and pluripotent stem cell-derived human hepatocytes. In some embodiments, the pluripotent stem cell-derived hepatocytes are selected from the group consisting of embryonic stem cell-derived hepatocytes or induced pluripotent stem cell-derived hepatocytes. In some embodiments, the embryonic fibroblasts are mouse embryonic fibroblasts or human embryonic fibroblasts. In some embodiments, the human hepatocytes are cultured for about 6 days to obtain a cell population comprising $CD44^+$ small hepatocyte progenitor cells.

In a second aspect, provided herein is a substantially pure, isolated population of $CD44^+$ small hepatocyte progenitor cells obtained according to the methods described herein. In some embodiments, the $CD44^+$ small hepatocyte progenitor cells proliferate in culture for at least 3 passages. In some embodiments, after 3 passages, the SHPCs retain at least 95% metabolic enzyme activity compared to metabolic enzyme activity of the starting human hepatocyte population. In some embodiments, the SHPCs are genetically engineered and comprise a heterologous nucleic acid.

In a third aspect, provided herein is a pharmaceutical composition comprising a small hepatocyte progenitor cell population obtained according to the methods described herein and a pharmaceutically acceptable carrier.

In a fourth aspect, provided herein is a method for treating a liver disease or injury in a patient, comprising administering to the patient a therapeutic dose of $CD44^+$ small hepatocyte progenitor cells obtained according to the methods described herein. In some embodiments, the disease or injury is selected from the group consisting of hepatitis, liver infection, cirrhosis of the liver, alpha-1-antitrypsin deficiency, Wilson's disease, inherited liver disease, chronic liver disease and acute liver damage.

In a fifth aspect, provided herein is a method for obtaining a population of mature human hepatocytes, the method comprising culturing the population of small hepatocyte progenitor cells obtained according to the method of claim 1 in the presence of sinusoidal endothelial cells in a culture medium that supports survival of sinusoidal endothelial cells and under conditions suitable for generation of mature human hepatocytes, whereby a cell population comprising mature hepatocytes is obtained. In some embodiments, the sinusoidal endothelial cells are human liver sinusoidal endothelial cells. In some embodiments, the culture medium comprises N2 and B27. In some embodiments, the culture medium comprising N2 and B27 further comprises dexamethasone and epidermal growth factor.

In a sixth aspect, provided herein is a method of obtaining a population of mature human hepatocytes, the method comprising culturing the population of small hepatocyte progenitor cells obtained according to the methods described herein in a culture medium comprising a MAPK inhibitor, whereby a cell population comprising mature hepatocytes is obtained. In some embodiments, the population of small hepatocyte progenitor cells is cultured in the presence of mouse embryonic fibroblasts or human embryonic fibroblasts. In some embodiments, the population of small hepatocyte progenitor cells is cultured in the presence of human sinusoidal endothelial cells. In some embodiments, the MAPK inhibitor is U0126. In some embodiments, the culture medium comprising a MAPK inhibitor additionally comprises N2 and B27. In some embodiments, the culture medium additionally comprises dexamethasone and epidermal growth factor.

In a seventh aspect, provided herein is a substantially pure, isolated population of genetically engineered mature hepatocytes derived from a genetically engineered small hepatocyte progenitor cell population obtained by the methods described herein.

In an eighth aspect, a cell culture medium comprises epidermal growth factor, Y27632, A083, CHIR99021, N2, and B27. In some embodiments, the cell culture medium comprises between about 10 ng/ml and about 200 ng/ml epidermal growth factor, between about 0.5 µM and about 50 µM Y27632, between about 0.05 µM and about 10 µM A083, between about 0.1 µM and about 20 µM CHIR99021, 1× N2, and 1× B27. In some embodiments, the cell culture medium additionally comprises dexamethasone, Oncostatin M, fetal bovine serum, insulin, nicotinamide, or combinations thereof. In some embodiments, the cell culture medium comprises 1 µM dexamethasone, 100 ng/ml epidermal growth factor, 10 µg/ml Oncostatin M, 20% fetal bovine serum, 2 µg/ml insulin, 100 nM nicotinamide, 10 µM Y27632, 0.5 µM A083, 3 µM CHIR99021, 1× N2 and 1× B27.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF DRAWINGS

The patent or patent application file contains at least one drawing in color. Copies of this patent or patent application publication with color drawings will be provided by the Office upon request and payment of the necessary fee.

DETAILED DESCRIPTION OF THE INVENTION

Figure 1:
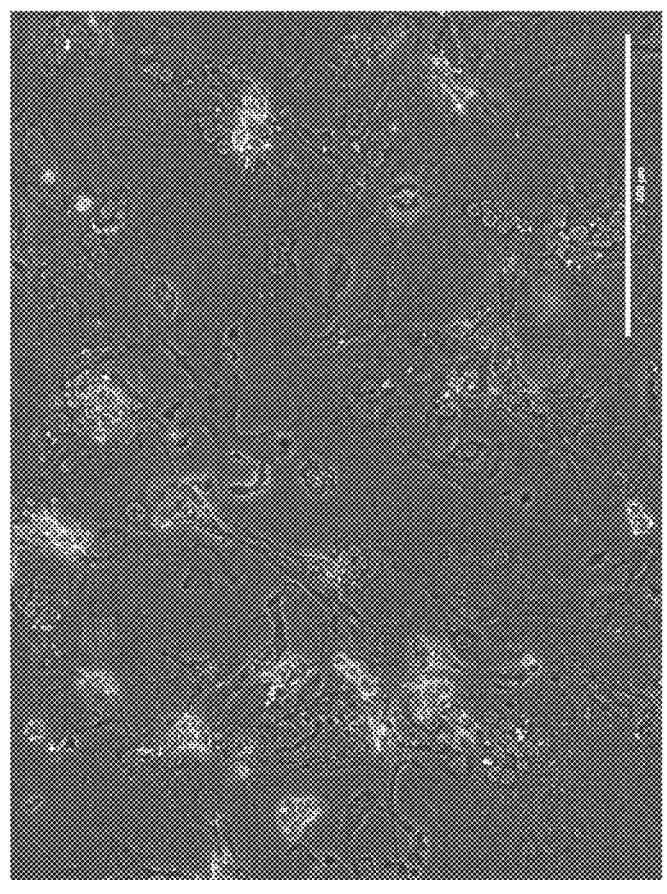
FIG. 1 shows maintenance of small hepatocyte progenitor cells (SHPCs). SHPCs developing from mature hepatocytes (MHs) (derived from a 19 year old male donor, batch HU8295) on day 6 following plating on mouse embryonic fibroblasts (MEFs) in SHPC medium (left) whereas those same cells plated on MATRIGEL™ in hepatocyte growth medium de-differentiate completely (right).
Figure 1:
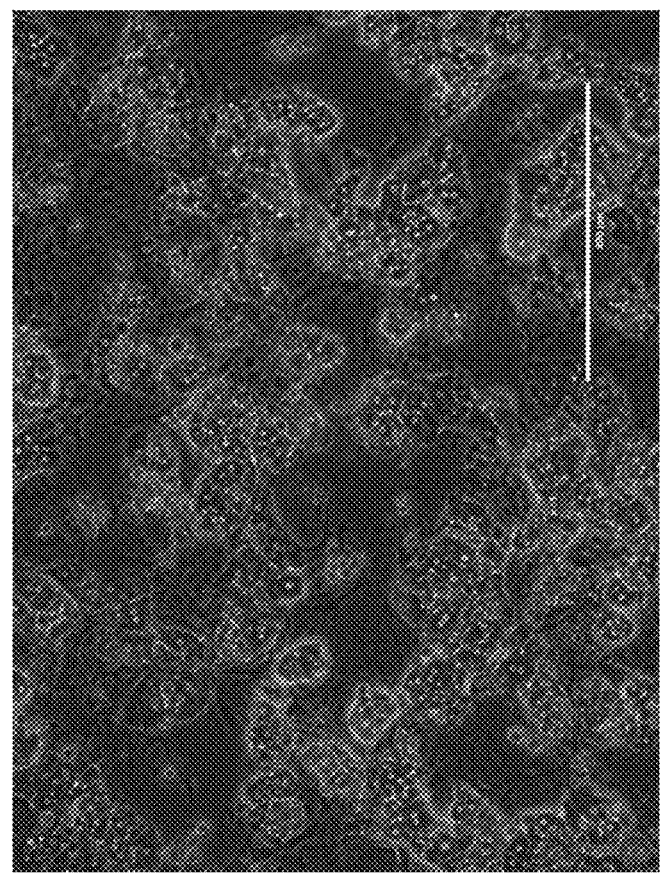

The present disclosure is based, at least in part, on the Inventors' development of protocols for deriving and culturing small hepatocyte progenitor cells (SHPCs) from mature primary human hepatocytes. In particular, when mature human hepatocytes are plated on embryonic fibroblasts and cultured in the presence of N2 and B27, populations of SHPCs can be generated. Based on these discoveries, the present invention provides methods for producing and expanding human SHPCs for use in methods for generating stable and expandable populations of mature hepatocytes and for toxicity and metabolic testing applications.

As used herein, "small hepatocyte progenitor cells (SHPCs)" are mature hepatocyte precursor cells characterized by expression of CD44. SHPCs have a small round morphology with clear nuclei resembling mature adult hepatocytes but smaller in size. SHPCs are typically between about 8 µm and about 20 µm in diameter (e.g., larger than about 8 µm but less than 20 less than 18 less than 15 less than 12 or less than 10 µm). In contrast, primary human hepatocytes in 2-dimensional culture are typically about 30 µm in diameter. SHPCs can originate by partial de-differentiation from mature hepatocytes when needed, such as upon liver injury or disease, to proliferate and restore liver mass.

The present invention also provides methods of maturing SHPCs into mature hepatocytes.

Methods

In a first aspect, provided herein are in vitro methods for obtaining SHPCs in culture. In exemplary embodiments, the methods comprise co-culturing human hepatocytes with embryonic fibroblasts in a culture medium to produce SHPCs. In some cases, the human hepatocytes are cultured in medium that comprises dexamethasone, epidermal growth factor, Oncostatin M, fetal bovine serum, insulin, nicotinamide, Y27632, A083, CHIR99021, N2, and B27 in amounts effective and for lengths of time sufficient to direct partial de-differentiation of mature human hepatocytes to SHPCs. Hepatocytes are cultured in the culture medium for about 6 days (e.g., 5 days, 6 days, 7 days, 8 days). In some embodiments, hepatocytes are co-cultured with fibroblasts in culture medium comprising or consisting essentially of DMEM/F12 culture medium, L-ascorbic acid-2-phosphate magnesium, sodium selenium, insulin, NaHCO$_3$, transferrin, dexamethasone, epidermal growth factor, Oncostatin M, fetal bovine serum, insulin, nicotinamide, Y27632, A083, CHIR99021, N2, and B27 for about 6 days. In some embodiments the culture medium comprises or consists essentially of DMEM/F12 culture medium, L-ascorbic acid-2-phosphate magnesium (64 ng/ml), sodium selenium (14 ng/ml), insulin (20 mg/l), NaHCO$_3$ (543 µg/ml), transferrin (10.7 µg/ml), dexamethasone (1 µM), epidermal growth factor (100 ng/ml), Oncostatin M (10 µg/ml), 20% fetal bovine serum, insulin (2 µl/ml), nicotinamide (100 mM), Y27632 (10 µM), A083 (0.5 µM), CHIR99021 (3 µM), N2 (1×), and B27 (1×). In some embodiments, the embryonic fibroblasts are mouse embryonic fibroblasts (MEFs). The culturing can take place on any appropriate surface (e.g., in two-dimensional or three-dimensional culture).

The hepatocytes for use in the present methods may be primary human hepatocytes or pluripotent stem cell-derived human hepatocytes. Hepatocytes are characterized by expression of albumin (ALB), alpha-fetoprotein, HNF4A, SERPINA1, CYP2E1, CYP3A4, CYP3A5, CYP1A1, CYP1B1, UGT1A1, UGT1A6, and UGT1A9.

The term "primary hepatocyte" refers to a hepatocyte cell obtained by isolating cells from liver tissue and culturing ex vivo. Primary hepatocytes de-differentiate in culture in a very short time and do not grow in culture without additional manipulation.

"Fresh primary hepatocytes" or "uncultured primary hepatocytes" refers to commercially available cryopreserved hepatocytes that were not thawed or cultured once received and before being placed into culture for use in the disclosed methods.

The pluripotent stem cells employed in methods that differentiate pluripotent stem cells into hepatocytes can be embryonic stem cells or induced pluripotent stem cells. Such methods are described, for example, in U.S. Patent Publication No. 2018/0015126A1.

The fibroblasts used in co-culture with the mature hepatocytes may be human embryonic fibroblasts (Kibschuli et al., Stem Cell Res, 2011, 6(1):70-82) or mouse embryonic fibroblasts. Mouse embryonic fibroblasts or human embryonic fibroblasts may be obtained from any suitable source. A skilled artisan may be motivated to use human embryonic fibroblasts when the SHPCs are needed for xeno-free clinical use.

For several of the biological markers described herein, expression will be low or intermediate in level. While it is commonplace to refer to cells as "positive" or "negative" for a particular marker, actual expression levels are a quantitative trait. The number of molecules on the cell surface can vary by several logs, yet still be characterized as "positive."

Accordingly, characterization of the level of staining permits subtle distinctions between cell populations. Expression levels can be detected or monitored by flow cytometry, where lasers detect the quantitative levels of fluorochrome (which is proportional to the amount of cell surface antigen bound by the antibodies). Flow cytometry or fluorescence-activated cell sorting (FACS) can be used to separate cell populations based on the intensity of antibody staining, as well as other parameters such as cell size and light scatter. Although the absolute level of staining may differ with a particular fluorochrome and antibody preparation, the data can be normalized to a control.

Any appropriate method can be used to detect expression of biological markers characteristic of cell types described herein. For example, the presence or absence of one or more biological markers can be detected using, for example, RNA sequencing (e.g., RNA-seq), immunohistochemistry, polymerase chain reaction, quantitative real time PCR (qRT-PCR), or other technique that detects or measures gene expression. RNA-seq is a high-throughput sequencing technology that provides a genome-wide assessment of the RNA content of an organism, tissue, or cell. Alternatively, or additionally, one may detect the presence or absence of, or measure the level of, one or more biological markers of SHPCs using, for example, Fluorescence in situ Hybridization (FISH; see WO98/45479 published October, 1998), Southern blotting, Northern blotting, or polymerase chain reaction (PCR) techniques, such as qRT-PCR. In exemplary embodiments, a cell population obtained according to a method provided herein is evaluated for expression (or the absence thereof) of biological markers of SHPCs such as CD44. Preferably, SHPCs express the small hepatocyte progenitor cell markers CD44 and one or more of the hepatocyte markers albumin (ALB), alpha-fetoprotein, SERPINA1, CYP2E1, CYP3A5, CYP1A1, CYP1B1, UGT1A1, UGT1A6, and UGT1A9. Quantitative methods for evaluating expression of markers at the protein level in cell populations are also known in the art. For example, flow cytometry is used to determine the fraction of cells in a given cell population that express or do not express biological markers of interest.

In a second aspect, provided herein are methods for maturing SHPCs to mature hepatocytes. Methods of maturing SHPCs to mature hepatocytes includes co-culturing SHPCs with sECs, culturing the SHPCs in the presence of a MAPK inhibitor, or co-culturing SHPCs with sECs in the presence of a MAPK inhibitor. In some embodiments, methods of maturing SHPCs to mature hepatocytes may also include forced expression of let-7 microRNA, as in the methods described in U.S. Patent Publication 2018/0015126A1.

In exemplary embodiments, a method of maturing SHPCs to mature hepatocytes includes co-culturing SHPCs with sECs and culturing in a medium that supports survival of sinusoidal endothelial cells and under conditions suitable for generation of mature human hepatocytes to obtain mature hepatocytes. In some embodiments, the culture medium comprises dexamethasone, epidermal growth factor, Oncostatin M, fetal bovine serum, insulin, nicotinamide, Y27632, A083, CHIR99021, N2, and B27 in amounts effective and for a length of time sufficient to obtain mature hepatocytes. SHPCs are cultured in the culture medium for at least about 2 days (e.g., at least about 2 days, 3 days, 4 days, 5 days, or longer). In some embodiments, SHPCs are co-cultured with sECs in culture medium comprising or consisting essentially of DMEM/F12 culture medium, L-ascorbic acid-2-phosphate magnesium, sodium selenium, insulin, NaHCO$_3$, transferrin, dexamethasone, epidermal growth factor, Oncostatin M, fetal bovine serum, insulin, nicotinamide, Y27632, A083, CHIR99021, N2, and B27 for at least about 3 days. In some embodiments the culture medium comprises or consists essentially of DMEM/F12 culture medium, L-ascorbic acid-2-phosphate magnesium (64 ng/ml), sodium selenium (14 ng/ml), insulin (20 mg/l), NaHCO$_3$ (543 µg/ml), transferrin (10.7 µg/ml), dexamethasone (1 µM), epidermal growth factor (100 ng/ml), Oncostatin M (10 µg/ml), 20% fetal bovine serum, insulin (2 µl/ml), nicotinamide (100 mM), Y27632 (10 µM), A083 (0.5 µM), CHIR99021 (3 µM), N2 (1×), and B27 (1×). In some embodiments, the SHPCs are derived from primary hepatocytes or pluripotent stem cell-derived hepatocytes by the methods described herein. In some embodiments, the sECs are primary human sECs. In some embodiments, the sECs are primary human liver sECs. The culturing can take place on any appropriate surface (e.g., in two-dimensional or three-dimensional culture). In some embodiments, the sECs are plated on vitronectin-coated plates and the SHPCs are plated on the sECs.

In exemplary embodiments, a method of maturing SHPCs to mature hepatocytes includes culturing SHPCs in a medium comprising a MAPK inhibitor to obtain mature hepatocytes. In some cases, the SHPCs are cultured in medium that comprises a MAPK inhibitor, dexamethasone, epidermal growth factor, Oncostatin M, fetal bovine serum, insulin, nicotinamide, Y27632, A083, CHIR99021, N2, and B27 in amounts effective and for a length of time sufficient to obtain mature hepatocytes. SHPCs are cultured in the culture medium for about 3 days (e.g., about 2 days, about 3 days, about 4 days). In some embodiments, the SHPCs are cultured in culture medium comprising or consisting essentially of DMEM/F12 culture medium, a MAPK inhibitor, L-ascorbic acid-2-phosphate magnesium, sodium selenium, insulin, NaHCO$_3$, transferrin, dexamethasone, epidermal growth factor, Oncostatin M, fetal bovine serum, insulin, nicotinamide, Y27632, A083, CHIR99021, N2, and B27 for about 3 days. In some embodiments the culture medium comprises or consists essentially of DMEM/F12 culture medium, a MAPK inhibitor, L-ascorbic acid-2-phosphate magnesium (64 ng/ml), sodium selenium (14 ng/ml), insulin (20 mg/l), NaHCO$_3$ (543 µg/ml), transferrin (10.7 µg/ml), dexamethasone (1 µM), epidermal growth factor (100 ng/ml), Oncostatin M (10 µg/ml), 20% fetal bovine serum, insulin (2 µl/ml), nicotinamide (100 mM), Y27632 (10 µM), A083 (0.5 µM), CHIR99021 (3 µM), N2 (1×), and B27 (1×). In some embodiments, the SHPCs are derived from primary hepatocytes or pluripotent stem cell-derived hepatocytes by the methods described herein. In some embodiments, the SHPCs are co-cultured with embryonic fibroblasts. In some embodiments, the SHPCs are co-cultured with sECs. The culturing can take place on any appropriate surface (e.g., in two-dimensional or three-dimensional culture).

Inhibitors of MAPK are known in the art and include, but are not limited to, for example, inhibitors of p38, mitogen activated and extracellular regulated kinase (MEK)1 and MEK2 protein kinases, for example, U0126 (a dual MEK1 & MEK2 inhibitor), PD098059 (a MEK1 inhibitor), and SB203580 (a p38 MAP kinase inhibitor), AZD6244 (MEK1 inhibitor), Trametinib (GSK1120212, MEK1/2 inhibitor) TAK 715, SB203580, SB202190, PD0325901, PD184352, SB239063, SB706504, and combinations thereof. In some embodiments, the MAPK inhibitor is U0126. In some embodiments, the MAPK inhibitor is PD09059. In some embodiments, the MAPK inhibitor is a combination of U0126 and PD09059.

Suitable concentrations of MAPK inhibitors used in the present methods and kits include, but are not limited to, about 10 nm to about 10 mM, alternatively about 10 nm to about 2 mM, alternatively about 10 nm to about 1 mM, alternatively from about 10 nm to about 500 alternatively from about 100 nm to about 2 mM, alternatively from about 100 nm to about 1000 alternatively from about 1 µM to about 200 alternatively about 1 µM to about 100 µM of the MAPK inhibitor. For example, in one embodiment, the concentration of MAPK is from about 5 µM to about 150 alternatively from about 5 µM to about 50 alternatively about 5 µM to about 10 µM. In a preferred embodiment, the MAPK inhibitor is used in an amount of about 10 µM.

Additional methods of maturing hepatocytes are known in the art, for example, in U.S. Patent Publication No. 2018/0015126. SHPCs generated by the methods described herein may be used in other methods known in the art for maturing hepatocytes.

In a some aspects, provided herein are methods for testing the potential toxicity of a compound. In one embodiment, such a method includes the steps of (a) exposing one or more hepatocytes produced by the methods described herein to the compound, and (b) monitoring the one or more hepatocytes for signs of toxicity. In another embodiment, such a method includes the steps of (a) exposing one or more hepatocytes produced by the methods described herein to the compound, wherein the compound is metabolized by the hepatocytes; (b) contacting the resulting metabolite(s) of the compound with one or more non-hepatocyte cells; and (c) monitoring the non-hepatocyte cells for any metabolite-induced changes. Non-limiting examples of non-hepatocyte cells that could be used in the method include neurons or cardiomyocytes.

In one embodiment, such a method for testing the potential toxicity of a compound includes the steps of (a) exposing one or more SHPCs produced by the methods described herein to the compound, and (b) monitoring the one or more SHPCs for signs of toxicity. In another embodiment, such a method includes the steps of (a) exposing one or more SHPCs produced by the methods described herein to the compound, wherein the compound is metabolized by the SHPCs; (b) contacting the resulting metabolite(s) of the compound with one or more non-hepatocyte cells; and (c) monitoring the non-hepatocyte cells for any metabolite-induced changes. Non-limiting examples of non-hepatocyte cells that could be used in the method include neurons or cardiomyocytes.

In some embodiments, the present disclosure provides methods of determining metabolites of a test compound. Such a method includes the steps of (a) exposing one or more SHPCs or hepatocytes produced by the methods described herein to the compound; and (b) determining which metabolites are produced by the hepatic processing of the compound. In addition to testing the toxicity of a test compound on the SHPCs or hepatocytes themselves, the hepatocyte medium containing the metabolite(s) of the test compound may be evaluated for toxicity or other effect upon cultures of non-hepatocytes.

For example, liver cell metabolites may be subsequently tested on cardiomyocytes (for cardiotoxicity testing) or on cultures of neurons (for neurotoxicity testing). Testing on the non-hepatocyte cells may occur either in a co-culture, or with a conditioned medium. This method may be used to test drugs that are not toxic themselves, but which may be converted to a toxic form by the liver. For example, certain liver metabolites of non-toxic compounds are known to block the hERG channel in the heart, causing arrhythmias.

However, the method is not limited by this example, and can be broadly applied to a variety of non-hepatocyte cell types.

Such methods include the step of monitoring the hepatocytes or non-hepatocytes for signs of potential toxicity. The cells need not be directly observed, and this step encompasses a variety of methods for assaying potential cellular damage or dysfunction caused by exposure to a test compound. Monitoring for signs of toxicity may include, without limitation, testing for the levels of certain biomarkers or gene expression products, testing cellular function, and directly observing the structure of the cells. As a non-limiting example, elevated levels of certain biochemical markers (e.g., alanine transferase, alkaline phosphatase, and bilirubin) can indicate hepatotoxicity. Furthermore, apoptosis, or morphological or neoplastic transformation of cells may result from induced toxicity. The method is not limited to any particular monitoring technique, and encompasses any such techniques used in the art.

In additional embodiments, SHPCs or hepatocytes generated by the methods described herein may be used to study drug-drug interaction. For example, SHPCs and hepatocytes produced by the methods described herein may be contacted with a drug and upregulation or inhibition of polymorphic cytochrome P450 enzymes (CYPs) can be measured. Upregulation or inhibition of CYPs will reduce or increase the effectiveness of a second compound originally metabolized through the particular CYP of interest.

Compositions

Provided herein is an isolated population of SHPCs generated by the methods described herein. The isolated population of SHPCs is capable of proliferating in culture for at least 3 passages, at least 5 passages, at least 7 passages, at least 10 passages, or at least 15 passages. In some embodiments, cells are passaged after about 3 days in culture. After at least 3 passages (e.g., at least 5 passages, at least 7 passages, at least 10 passages, or at least 15 passages), the population of SHPCs retains between about 85% and about 150% (e.g., 85%, 90%, 95%, 99%, 100%, 105%, 110%, 120%, 130%, 140%, or 150%) metabolic enzyme activity compared to a population of freshly thawed PPH from the same donor or a population of ES derived hepatocytes from which the SHPCs were differentiated. In some embodiments, after at least 3 passages (e.g., at least 5 passages, at least 7 passages, at least 10 passages, or at least 15 passages) the population of SHPCs retain at least 85% (e.g., at least 85%, at least 90%, at least 95%, at least 99%, at least 100%, at least 105%, at least 110%, at least 120%, at least 130%, at least 140%, or at least 150%) metabolic enzyme activity compared to a population of freshly thawed PPH from the same donor or a population of ES derived hepatocytes from which the SHPCs were differentiated. In some embodiments, the metabolic enzyme activity is measured by measurement of major acetaminophen metabolites produced when acetaminophen is cultured with the indicated cell population for about 1 hour. Phase I and Phase II metabolic enzymes of interest present in the isolated population of SHPCs are CYP3A4, CYP3A5, CYP2C9, CYP2E1, CYP2D6, CYP2C19, CYP1A1, CYP1B1, UGT1A1, UGT1A6, and UGT1A9.

In another aspect, provided herein is a genetically engineered SHPC produced by the methods described herein. Also provided herein is a genetically engineered mature hepatocyte differentiated from an SHPC produced by the methods described herein.

As used herein, the terms "genetically engineered" and "genetically modified" are used interchangeably and refer to a cell (e.g., prokaryotic or eukaryotic cell) that has been modified to comprise a non-naturally occurring nucleic acid molecule that has been created or modified by the hand of man (e.g., using recombinant DNA technology) or is derived from such a molecule (e.g., by transcription, translation, etc.). An SHPC or mature hepatocyte that contains an exogenous, recombinant, synthetic, and/or otherwise modified polynucleotide is considered to be a genetically modified cell and, thus, non-naturally occurring relative to any naturally occurring counterpart. In some cases, genetically modified cells contain one or more recombinant nucleic acids. In other cases, genetically modified cells contain one or more synthetic or genetically engineered nucleic acids (e.g., a nucleic acid containing at least one artificially created insertion, deletion, inversion, or substitution relative to the sequence found in its naturally occurring counterpart). Procedures for producing genetically engineered cells are generally known in the art, for example, as described in Sambrook et al, *Molecular Cloning, A Laboratory Manual (Fourth Edition)*, Cold Spring Harbor Press, Cold Spring Harbor, N.Y. (2012) and Doudna et al, *CRISPR-Cas, A Laboratory Manual*, Cold Spring Harbor Press, Cold Spring Harbor, N.Y. (2016), each of which is incorporated herein by reference.

In some cases, a cell's genome is modified (e.g., engineered) so that functional Phase I and Phase II hepatocyte metabolic enzyme encoding genes are up-regulated or down-regulated. In some embodiments, the cells are engineered to modify the metabolic pathway of the mature hepatocytes or SHPCs. Mature hepatocytes cannot be genetically engineered. However, SHPCs produced by the methods described herein can be genetically engineered and used to produce genetically engineered mature hepatocytes. SHPCs may be genetically engineered to facilitate identification of host factors that play a role in hepatitis virus life cycle. Additions genetically engineered SHPCs and mature hepatocytes derived therefrom can be used to investigate the role of nuclear receptors and CYPs in a candidate drug's metabolism and induction/inhibition of other metabolic pathways. Genetically engineered SHPCs and mature hepatocytes differentiated therefore can also be used to identify target genes involved in tumorigenesis and other liver diseases such as non-alcoholic fatty liver disease (NAFLD), non-alcoholic steatohepatitis (NASH), etc.

In another aspect, provided herein is a cell culture medium for obtaining SHPCs. The cell culture medium includes epidermal growth factor, Y27632, A083, CHIR99021, N2, and B27. In some embodiments, the cell culture medium includes between about 10 ng/ml and about 200 ng/ml (e.g., between about 20 ng/ml and about 180 ng/ml, between about 50 ng/ml and about 150 ng/ml, or between about 75 ng/ml and about 125 ng/ml) of epidermal growth factor. In some embodiments, the cell culture medium includes between about 0.5 µM and about 50 µM (e.g., between about 1 µM and about 40 µM, between about 2.5 µM and about 30 µM, between about 5 µM and about 20 µM, between about 7.5 µM and about 15 µM, or between about 9 µM and about 12 µM) of Y27632. In some embodiments, the cell culture medium includes between about 0.05 µM and about 10 µM (e.g., between about 0.1 µM and about 5 µM, between about 0.25 µM and about 2.5 µM, or between about 0.4 µM and about 1 µM) of A083. In some embodiments, the cell culture medium includes between about 0.1 µM and about 20 µM (e.g., between about 0.5 µM and about 18 µM, between about 0.75 µM and about 15 µM, between about 1 µM and about 10 µM, or between about 1.5 µM and about 5 µM) of CHIR99021. In some embodiments, the cell culture medium includes about 1× of N2 and B27 (e.g., 5 ml of 100× N2 and 10 ml of 50× B27 to make 500 ml of cell culture medium). In some embodiments, the cell culture medium additionally includes dexamethasone, Oncostatin M, fetal bovine serum, insulin, nicotinamide, or combinations thereof. In some embodiments, the cell culture medium includes epidermal growth factor, Y27632, A083, CHIR99021, N2, B27, dexamethasone, Oncostatin M, fetal bovine serum, insulin, and nicotinamide. In some embodiments, the cell culture medium includes 1 µM dexamethasone, 100 ng/ml epidermal growth factor, 10 µg/ml Oncostatin M, 20% fetal bovine serum, 2 µg/ml insulin, 100 nM nicotinamide, 10 µM Y27632, 0.5 µM A083, 3 µM CHIR99021, 1× N2 and 1× B27. In some embodiments, the cell culture medium additionally includes DMEM/F12 medium, L-ascorbic acid-2-phosphate magnesium, sodium selenium, NaHCO$_3$, and transferrin.

In another aspect, provided herein are therapeutic compositions that can contain SHPCs, mature hepatocytes, or other cell types obtained as described herein, as well as methods for making, and methods for using such therapeutic compositions.

In a further aspect, therefore, the present invention provides methods and compositions for cell transplantation, cell replenishment, cell or tissue replacement and enhancing liver regeneration and repair. The method can comprise providing to a subject in need thereof a therapeutically effective amount of SHPCs or mature hepatocytes derived according to methods provided herein, whereby providing SHPCs or mature hepatocytes treats the subject. Disorders requiring cell or tissue replacement and improving liver regeneration and repair include, without limitation, hepatitis liver infection, cirrhosis of the liver, liver metabolic disorders such as alpha-1-antitrypsin deficiency and Wilson's disease, acute liver damage (such as from drug overdose), and any other disorder or disease for which the stricken individual would benefit from SHPC or mature hepatocyte cell treatment or cell transplant.

Preferred subjects according to the present invention are mammals including, without limitation, humans and non-human primates, as well as rodents, canines, felines, ovines, porcines, equines, and bovines. In some cases, a substantially pure population of SHPCs or mature hepatocytes is obtained using a pluripotent cell (e.g., induced pluripotent stem cell) of the subject in need of treatment. However, a substantially pure population of SHPCs or mature hepatocytes also can be obtained using pluripotent stem cells of, preferably, a syngeneic or allogeneic donor. Less preferably, a xenogeneic donor is used.

Any appropriate dosage can be used for a therapeutic method provided herein. The cell dose will depend on the extent and severity of the liver disorder or disease but a suitable range is from about $1 \times 10^8$ cells/patient to about $1 \times 10^{10}$ cells/patient per dose. In some cases, SHPCs or mature hepatocytes obtained as described herein are co-administered to a subject with other cell types including, for example, sECs.

After administering the cells into the subject, the effect of the treatment method may be evaluated, if desired, using any appropriate method known to practitioners in the art. The treatment may be repeated as needed or required. Following treatment according to the methods provided herein, the treated subject can be monitored for any positive or negative changes in liver disorder or disease being treated. In a preferred embodiment, an increase in liver metabolism is a result of engraftment of SHPCs or mature hepatocytes following administration of the said cells.

Administration of a therapeutically effective amount of SHPCs or mature hepatocytes into the recipient subject is generally effected using methods well known in the art, and usually involves directly injecting or otherwise introducing a therapeutically effective amount of SHPCs or mature hepatocytes into the subject using clinical tools known to those skilled in the art. For example, introduction of SHPCs or mature hepatocytes of the present invention can be effected locally or systemically via intravascular administration, such as intravenous, intramuscular, or intra-arterial administration, intraperitoneal administration, and the like. Cells can be injected into an infusion bag (e.g., Fenwal infusion bag (Fenwal, Inc.)) using sterile syringes or other sterile transfer mechanisms. The cells can then be immediately infused via IV administration over time, such as 15 minutes, into a free flow IV line into the patient. In some embodiments, additional reagents such as buffers or salts are provided to the recipient subject concurrently with the cells.

In exemplary embodiments, SHPCs or mature hepatocytes of the present invention are provided to the subject as a pharmaceutical composition comprising the cells and one or more pharmaceutically acceptable carriers, buffers, or excipients. The pharmaceutical composition for administration must be formulated, produced, and stored according to standard methods that provide proper sterility and stability. A pharmaceutical composition of the present invention may also comprise one or more growth factors or cytokines (e.g., angiogenic cytokines) that promote the survival or engraftment of transplanted cells, promote angiogenesis, modulate the composition of extracellular or interstitial matrix, and/or recruit other cell types to the site of transplantation.

Regarding methods of treating liver disorders, the SHPCs or hepatocytes produced by the disclosed methods may be used either short term or long term in patients wherein an orthotopic liver transplant would be desirable. Transplantation of SHPCs or hepatocytes may save many lives, as there is a severe shortage of livers for transplantation, resulting in large number of deaths to patients on liver transplant waiting lists. For example, SHPCs or hepatocytes could be used for treatment of liver metabolic disorders such as alpha-1-antitrypsin deficiency and Wilson's disease, where in severe cases, orthotopic liver transplant is currently the only recourse. Furthermore, in cases of acute liver damage (such as from drug overdose), SHPC or hepatocyte transplantation may also save lives. Finally, SHPC or hepatocyte transplantation may help people on transplant waiting lists live long enough to receive an organ (i.e., bridge transplantation).

In another aspect, SHPCs produced by the methods described herein may be used to generate bioartificial livers. Discarded or donor livers may be decellularized by methods such as perfusion with detergents then recellularized using SHPCs generated by the methods described herein. See, for example, Mazza et al ("Decellularized human liver as natural 3D-scaffold for liver bioengineering and transplantation," Sci Rep 2015, 5:13079) which describes the synthetic in vitro growth of cells in a decellularized human liver matrix.

In another aspect, SHPCs produced by the methods described herein may be used to fabricate extra-corporeal liver assist devices to carryout liver function outside the body for example during a liver transplant or liver failure. Similar extra-corporeal devices include heart-lung machines that can perform the function of both heart and lungs using transplantation.

In another aspect, the present invention provides an in vitro culture of SHPCs to proliferate or grow an organoid, scaffold, or recellularized organ for transplant into a subject.

In another aspect, cell populations comprising SHPCs generated by the methods described herein are used in drug-drug interaction, drug metabolism, and toxicity testing. SHPCs may be cultured with one or more small molecule, macromolecule, biologic, RNA, DNA, or other drug candidates to measure and observe metabolites produced, rate of metabolism, and major metabolic pathways active for the given drug or drug candidates. SHPCs may be cultured with one or more small molecule, macromolecule, biologic, RNA, DNA, or other drug candidates to measure and observe drug toxicity. SHPCs may be cultured with two or more small molecule, macromolecule, biologic, RNA, DNA, or other drug candidates to study drug-drug or multidrug interactions.

The present invention has been described in terms of one or more preferred embodiments, and it should be appreciated that many equivalents, alternatives, variations, and modifications, aside from those expressly stated, are possible and within the scope of the invention.

EXAMPLE 1

The embodiment described here demonstrates the derivation, culture and maturation of SHPCs.

Materials and Methods

Primary Adult Human and Embryonic Stem Cell-Derived Hepatocytes—

Primary human hepatocytes (PHH) were purchased from Thermo Fisher Scientific (Cat #HMCPMS); one donor was a 19 year old Caucasian male, (Lot #HU8295), one was a 34 year old Caucasian female (Lot #Hu1962), and one was a 23 year old female (Lot #8290). Human embryonic stem cell-derived hepatocytes were generated by CDI (Madison, Wis.) from a dual reporter H9 clone expressing GFP from the Albumin promoter and TdTomato from the AFP promoter.

Mef Culture—

Mouse embryonic fibroblasts (MEFs) were obtained from E13.5 embryos of pregnant CD-1 female mice (purchased from Charles River Laboratories) 13 days post plugging, where plugging day is considered day 0.5. MEFs were cultured to passage 1-passage 3 (p1-p3) in growth medium (DMEM, supplemented with 10% heat-inactivated fetal bovine serum, 1% nonessential amino acid solution) and irradiated with a dose of 80Gy using a Mark I 137Cs irradiator (from J. L. Shepherd and Associates). Irradiated MEFs were seeded onto 0.1% gelatin coated plates at a concentration of $1.8\times10^5$ cells/mL to be used for culturing SHPCs.

SHPC Derivation and Culture—

Primary human adult and embryonic stem cell-derived hepatocytes (ESC-hepatocytes) were cultured on MEFs in SHPC medium. SHPC medium is E6 medium (DMEM/F12 medium, L-ascorbic acid-2-phosphate magnesium (64 mg/l); sodium selenium (14 μg/l); insulin (20 mg/l); NaHCO₃ (543 mg/l); and transferrin (10.7 mg/l), Chen et al., Nature Methods 2011 8(5):424-9) supplemented with Dexamethasone (1 μM), Epidermal growth factor (100 ng/ml), Oncostatin M (10 μg/ml), 20% Fetal bovine serum, insulin (2 μl/ml), Nicotinamide (100 mM), Y27632 (10 μM), A 083 (0.5 μM), CHIR 99021 (3 μM), N2 and B27 (1×—5 ml of 100× N2 and 10 ml of 50× B27 is used to make 500 ml of SHPC medium). PHH-SHPCs appeared about 6 days post PHH plating on MEFs in SHPC medium and are first passaged after 12-14 days. ES-SHPCs appear about 3 days post plating on ES-hepatocytes and are first passaged 6-8 days later. In both cases, morphologically dedifferentiated colonies were picked before passaging. Cells were passaged 1:3 every 3 days for PHH-SHPCs and 1:6 for ES-SHPCs.

Primary Human Sinusoidal Endothelial Cell Culture—

Primary human sECs were obtained from Cell Systems and cultured on vitronectin coated plates in endothelial cell basal medium 2 (EBM™-2) supplemented with endothelial growth medium 2 (EGM™-2) (Lonza).

RNA-Seq (LM-Seq)—

Total RNA was qualified with Life Technologies Qubit fluorometer (Q32857) and Agilent Bioanalyzer (G2940CA). Total RNA was used to prepare indexed cDNA libraries with the Ligation Mediated Sequencing (LM-Seq) protocol (Hou, Z et al. 2015). Final indexed cDNA libraries were pooled with forty-four uniquely indexed LM-Seq cDNA libraries per lane and sequenced on an Illumina HiSeq 3000.

SHPC Engraftment in Immunodeficient Mice—

Female (genotype sp/sp;ko/ko;tg/wt, model number 12907-F) Tk-NOG mice were purchased for transplantation experiments from Taconic Biosciences. Mice were maintained on NIH #31M Rodent Diet and 9-12 week old mice were used for transplantation. Mice were pretreated with ganciclovir (diluted with 0.9% saline, 50 mg/kg body weight in a total volume of 200 intraperitoneally) 14 and 7 days prior to transplantation. $1\times10^6$ cells in 100 μL 1×phosphate-buffered saline were directly injected into the spleen. Survival and body weight of mice were monitored during 9 weeks following which they were euthanized and their livers harvested for histologic and flow analyses to assess percentage engraftment.

Monitoring Engraftment Via Human Albumin ELISA—

Mouse blood was collected retro-orbitally and plasma was separated by two-step centrifugation. The blood samples were first centrifuged at 1500×g for 20 min at 4° C., following which the supernatant was collected and centrifuged again at 1500×g for about 10 min at 4° C. The supernatant, plasma, was collected and stored at −80° C. for ELISA. Human albumin in mouse blood was quantified by an enzyme-linked immunosorbent assay (ELISA) kit from Bethyl Laboratories (cat #E88-129).

Metabolic Enzyme Activity—

Acetaminophen was added to cultures of HU1962 PHHs, HU1926 SHPCs, HU8295 PHHs, HU8295 SHPCs, and control HepG2 cells. After 1 hour, the culture was assayed for production of acetaminophen glucuronide (APAP-glu, FIG. 16) and acetaminophen sulfate (APAP-Sul, FIG. 18) to measure phase II metabolism and production of acetaminophen glutathione (APAP-GSH, FIG. 17) to measure phase I and phase II metabolism. PHHs were cultured with acetaminophen and assayed immediately after thawing. SHPCs were cultured with acetaminophen and assayed after 3 passages.

Results

SHPC Derivation and Culture—

SHPCs have been described in rat (1) and these cells have been shown to originate by partial de-differentiation from mature hepatocytes (MHs) upon hepatectomy/chemically simulated injury to restore liver mass (3). Adult mouse liver derived MHs have also been driven to proliferate in vitro using three small molecules, Y27632, A 083 and CHIR 99021 (named YAC medium) (5). Neither isolation, culture, nor proliferation of SHPCs from humans has been successful in vitro. Attempts to use the cell culture medium and feeder layer described by Katsuda et al. for generation of mouse SHPCs were unsuccessful when used with primary human hepatocytes and did not produce stable proliferative human SHPCs. Cells generated using the culture conditions described by Katsuda died within a few days whereas the SHPCs generated by the method described herein survive and proliferate for at least 3 passages.

Perfusion of hepatocytes from human livers mirrors an injury and we hypothesized that this should prime the hepatocytes to generate proliferating SHPCs in culture, if provided with the right conditions. Since SHPCs originate from de-differentiation of MHs and represent an undifferentiated, stem cell-like population, to generate SHPCs from human MHs, we cultured them on MEFs that support culture of undifferentiated cells. To induce proliferation of SHPCs, we also provided the three small molecules that have been shown to induce proliferation of mouse hepatocytes (YAC). Further, we also included epidermal growth factor (EGF) that is known to induce hepatocyte proliferation along with N2 and B27, supplements that support adult stem cell culture.

Figure 2:
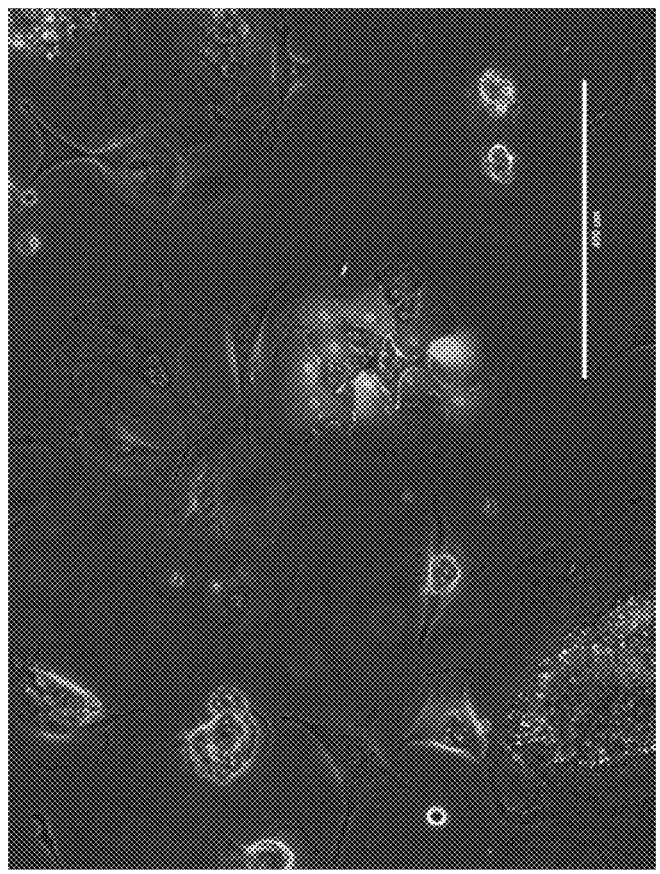
FIG. 2 shows SHPCs obtained from a dual reporter (expressing GFP and TdTomato from albumin and alpha feto-protein promoters respectively) H9 clone embryonic stem cell-derived hepatocytes (ESC-hepatocytes) plated on MEFs in SHPC medium. Their origin from mature hepatocytes is confirmed by GFP expression from the albumin reporter.
Figure 2:
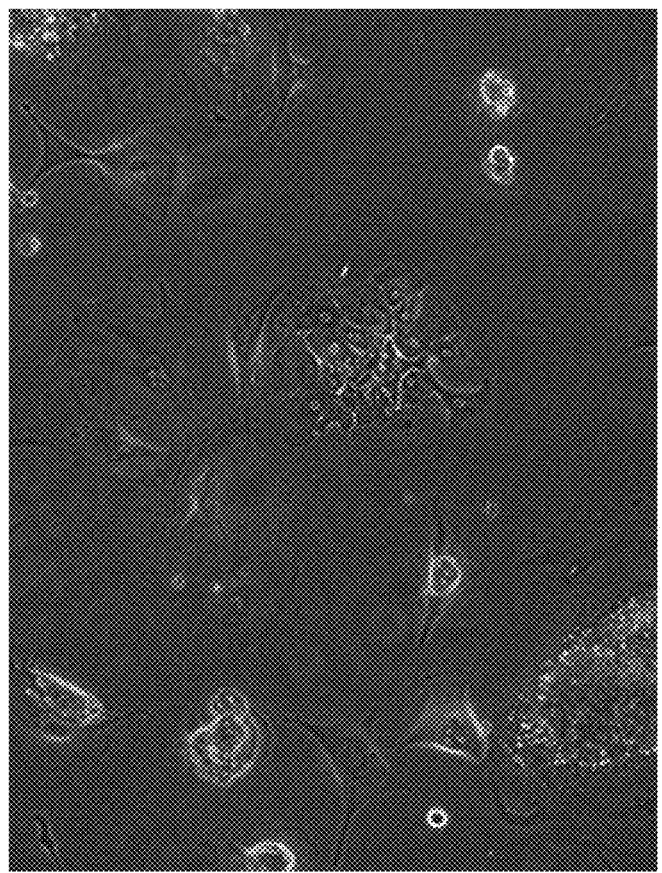
Figure 3:
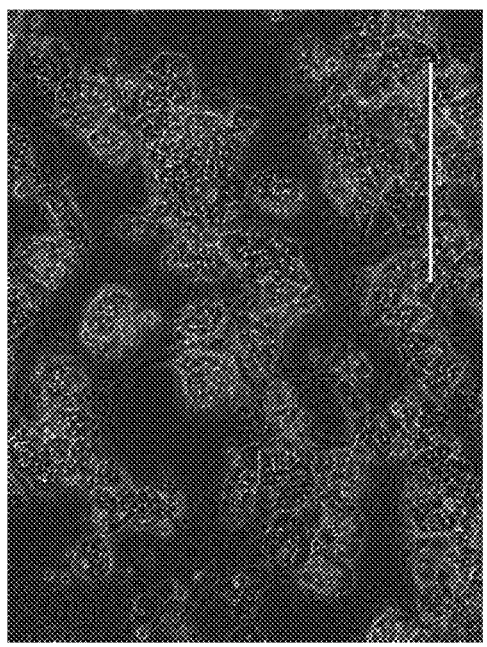
FIG. 3 shows SHPCs passaged on MEFs in SHPC medium (Passage 1 (P1), top, derived from a 19 year old male donor, batch HU8295). SHPCs derived from dual reporter clone, passage 2 (P2). Phase contrast (bottom left) and albumin reporter (bottom right).
Figure 3:
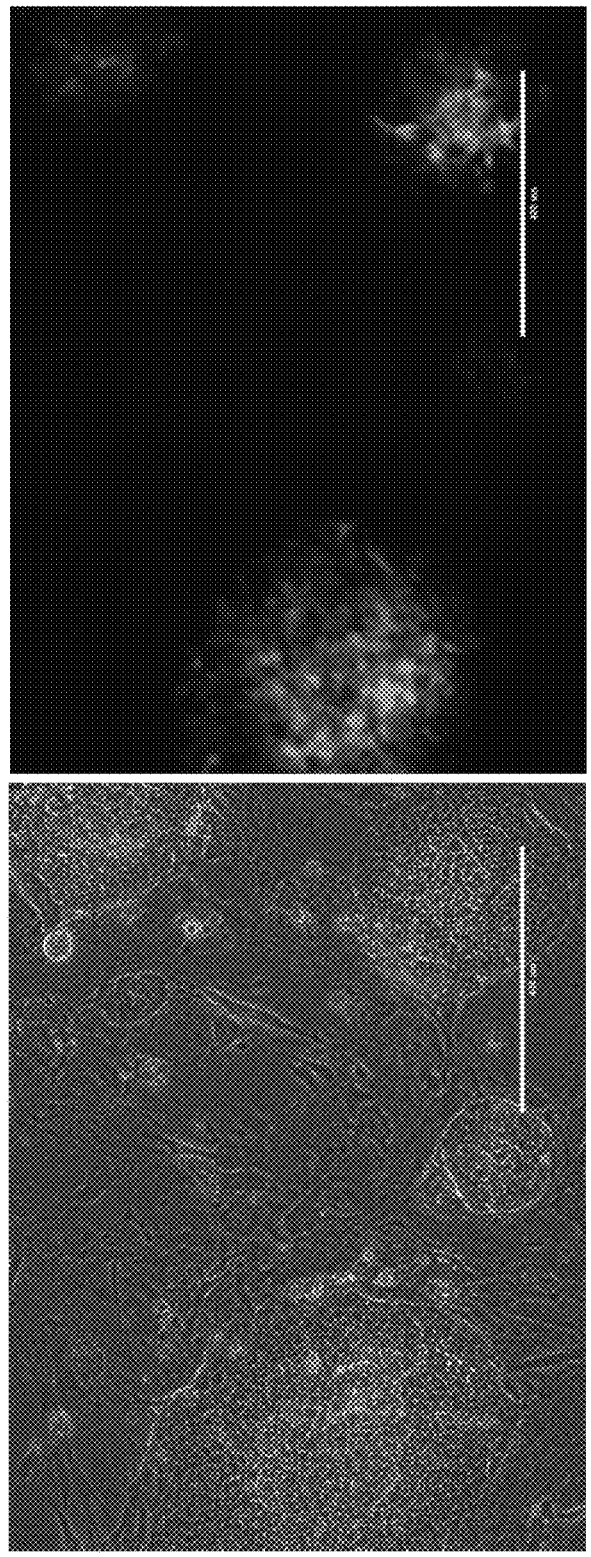

We thawed, washed and seeded primary human adult hepatocytes (one male, batch HU8295 and one female batch HU1962, Thermo Fisher) and embryonic stem cell-derived dual reporter hepatocytes on MEFs in SHPC medium ($2\times10^6$ cells/10 cm dish). Between 6 and 7 days post plating, small round SHPCs with clear nuclei were observed (FIG. 1) whereas control cells (plated on MATRIGEL™ coated plates in a commercial hepatocyte growth medium obtained from Promocell) showed a completely de-differentiated morphology wherein the cells are larger and flatter than mature adult hepatocytes. SHPCs displayed typical hepatocyte morphology, albeit much smaller than the primary adult hepatocytes (PHHs) from which they originated. We confirmed the origin of SHPCs from mature PHHs by observing their formation from albumin reporter expressing hepatocytes derived from the dual clone (FIG. 2) as has been reported in rats. These hepatocytes were also amenable to passaging by dissociating in 0.5% Trypsin-EDTA and passing through a 40 µm filter to eliminate MEFs. SHPCs maintained their morphology, albumin expression and proliferative capacity upon passaging (FIG. 3).

SHPC Maturation In Vitro—

Figure 4:
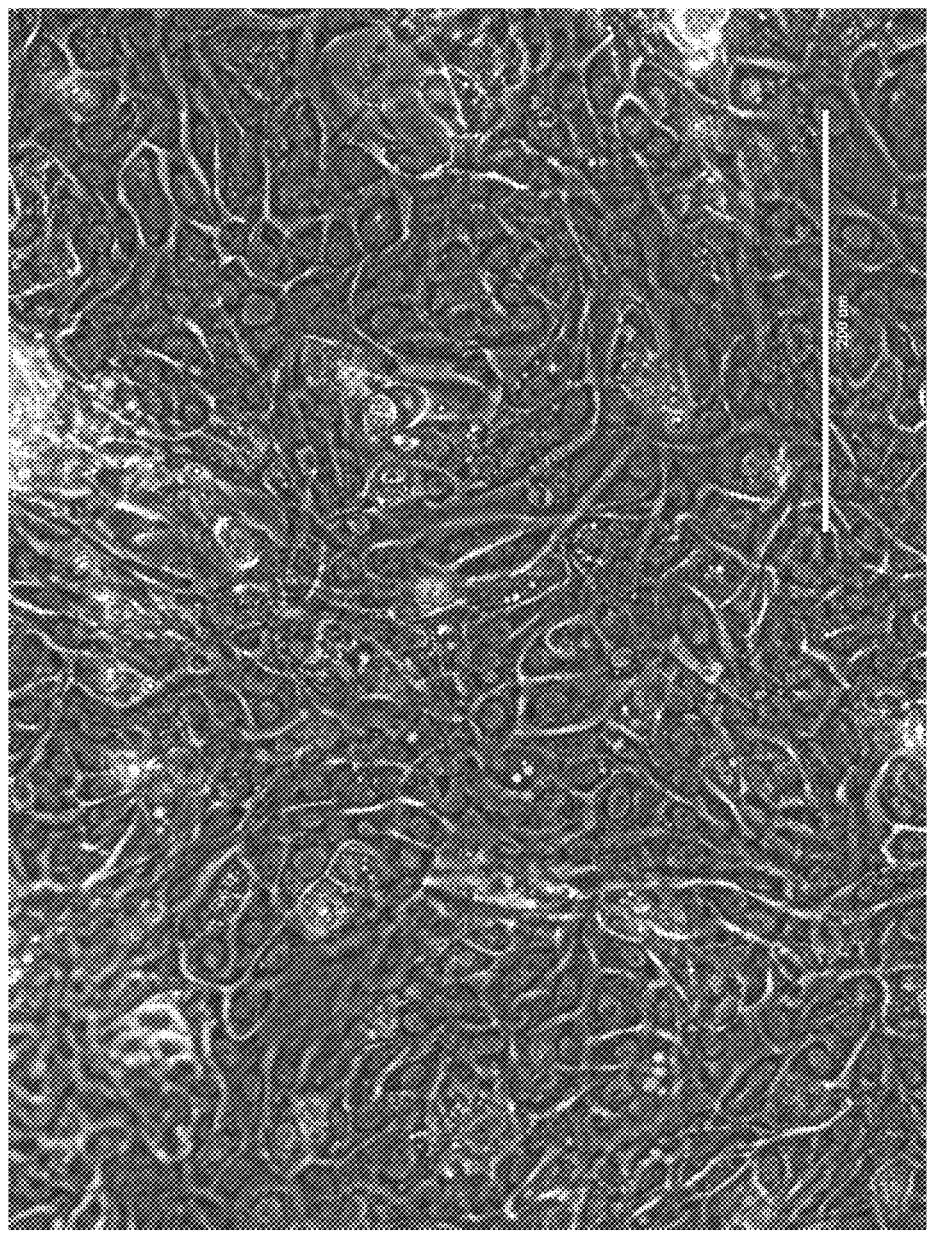
FIG. 4 shows SHPCs obtained from ESC-hepatocytes passaged on sinusoidal endothelial cells (sECs) display extensive bile canalicular structures between one to two cells as seen in vivo in hepatic chords.
Figure 5:
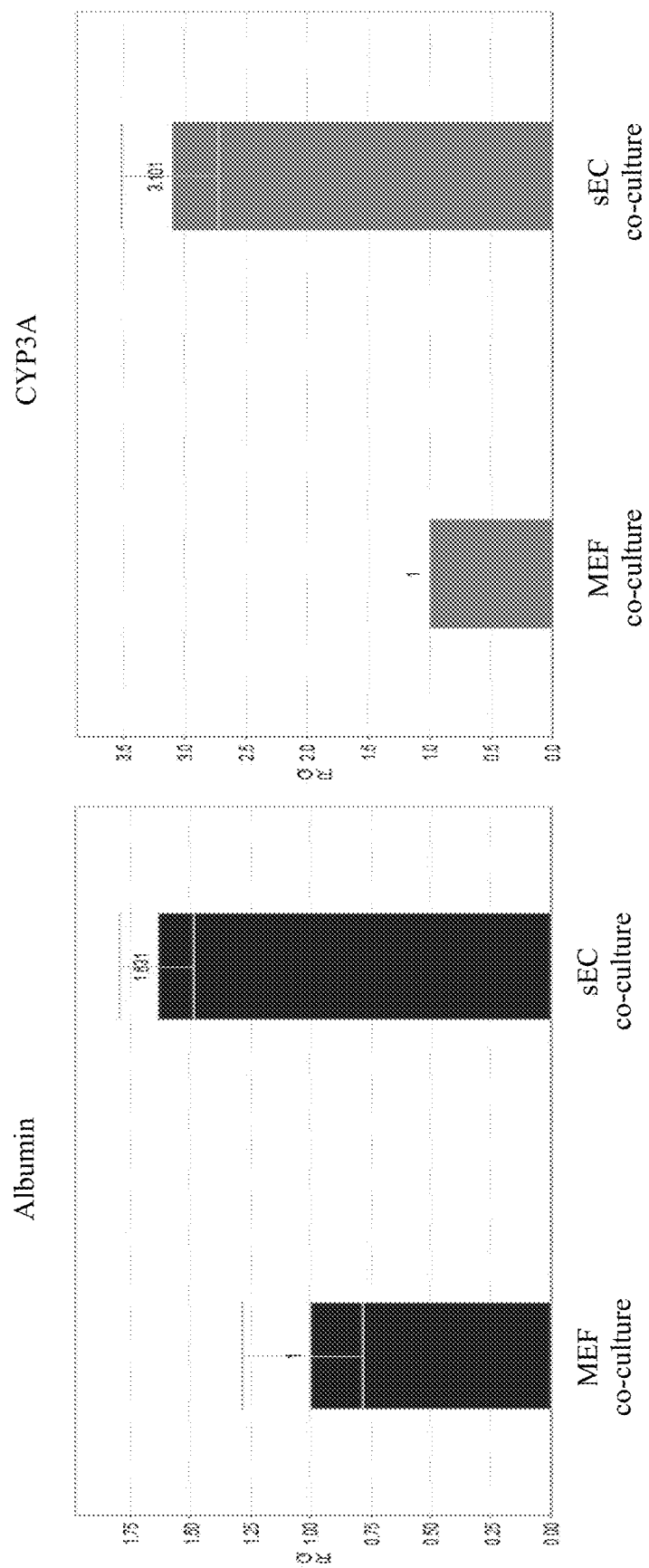
FIG. 5 shows co-culture of SHPCs derived from ESC-hepatocytes with sECs produces mature hepatocytes as evidenced by an increase in the relative quantity (RQ) of albumin (left) and CYP3A (right) expression.

Since SHPCs represent a de-differentiated form of MHs, we tried to mature them in vitro. SHPCs arise in hepatectomized livers and it has been shown that SHPCs proliferate first after the injury followed by proliferation of sECs. Further, it has been shown that these proliferating sECs secrete hepatocyte growth factor, a known agent that promotes hepatocyte maturation (6). We hypothesized that sECs play a role in maturation of SHPCs in vivo and co-cultured sECs with the SHPCs. SHPCs derived from ESC-hepatocytes were co-cultured in SHPC medium with either MEFs or sECs. Cells cultured with sECs, unlike those cultured on MEFs, showed pronounced bile canalicular structures between every one to two cells as seen in in vivo hepatic chords (FIG. 4). Cells from each of the MEF and sEC co-cultures were FAC sorted based on albumin promoter expression and QPCR of albumin and CYP3A (an important drug metabolizing enzyme) was performed. Albumin increased ~2-fold in cells co-cultured with sECs and CYP3A increased 3-fold confirming maturation of SHPCs in vitro (FIG. 5).

We had previously shown that MAPK inhibitors inhibit in vitro de-differentiation of mature primary hepatocytes and to mature a de-differentiated cell line. We derived SHPCs from adult mouse liver and treated them with the MAPK inhibitor U0126. RNA-Seq showed U0126 to mature the SHPCs as evidenced by increase in expression of mature genes coupled with decrease in fetal hepatic genes (Table 2).

TABLE 2

MAP kinase inhibition by U0126 matures mouse proliferating hepatocytes

| GENE | VEHICLE TREATED MOUSE ADULT PROLIFERATING HEPATOCYTES | U0126 TREATED MOUSE ADULT PROLIFERATING HEPATOCYTES |
|---|---|---|
| Albumin | 6523 | 11379 |
| CYP1A1 | 36 | 1447 |
| CYP1A2 | 1 | 78 |

TABLE 1

Gene expression values (RNA-Seq) of uncultured primary human hepatocytes and SHPCs derived from a male (HU8295) and a female (HU8290) donor. Also included are gene expression measurements of PHH from one donor (HU8290) cultured for 72 hours. Results from ES dual reporter hepatocytes and dual reporter SHPCs are also shown. Data show expression of hepatic markers and xenobiotic metabolism genes necessary for drug toxicity testing, albeit at lower levels than fresh uncultured primary hepatocytes.

| Gene | Dual reporter ES hepatocytes | Dual Reporter SHPCs | Uncultured HU8290 PPH | HU8290 Cultured 72 Hours | HU8290 SHPC | Uncultured HU8295 PPH | HU8295 SHPC | Gene type |
|---|---|---|---|---|---|---|---|---|
| ALB | 39376.26 | 35357.04 | 154088.63 | 3296.66 | 3409.86 | 50870.7 | 1785.05 | Hepatocyte marker |
| AFP | 40549.13 | 273.38 | 1.04 | 2.49 | 71.03 | 17.79 | 5.28 | Hepatocyte marker |
| CD44 | 10.57 | 149.26 | 0.35 | 64.98 | 176.98 | 0 | 54.66 | SHPC marker |
| HNF4A | 15.2 | 37.82 | 8.89 | 114.18 | 96.19 | 15.12 | 0.74 | Hepatocyte marker |
| SERPINA1 | 4897.39 | 28569.59 | 1832.96 | 2421.04 | 11813.24 | 18254.51 | 1545.3 | Hepatocyte marker |
| CYP3A4 | 20.58 | 67.19 | 40.89 | 1.38 | 0.1 | 14.77 | 0.22 | Phase I enzyme |
| CYP3A5 | 37.79 | 40.56 | 1682.01 | 35.47 | 226.57 | 32.37 | 81.92 | Phase I enzyme |
| CYP2C9 | 57.35 | 311.98 | 1091.52 | 92.19 | 8.03 | 652.99 | 38.45 | Phase I enzyme |
| CYP2E1 | 0.35 | 586.67 | 3340.11 | 1.01 | 1281.41 | 2556.93 | 251.45 | Phase I enzyme |
| CYP2D6 | 1.59 | 0.62 | 101.71 | 0 | 0.27 | 59.26 | 0 | Phase I enzyme |
| CYP2C19 | 7.85 | 52.69 | 175.24 | 28.32 | 3.31 | 3.94 | 0 | Phase I enzyme |
| CYP1A1 | 34.21 | 20.53 | 0 | 0 | 14.04 | 0.15 | 4.1 | Phase I enzyme |
| CYP1B1 | 1.26 | 2.74 | 3.89 | 0.26 | 104.34 | 2.18 | 48.44 | Phase I enzyme |
| UGT1A1 | 25.93 | 783.37 | 0 | 33.19 | 2.11 | 0 | 30.38 | Phase II enzyme |
| UGT1A6 | 50.92 | 629.48 | 1619.14 | 724.11 | 538.15 | 400.17 | 270.45 | Phase II enzyme |
| UGT1A9 | 9.43 | 153.45 | 360.43 | 121.22 | 73.98 | 43.08 | 27.6 | Phase II enzyme |

TABLE 2-continued

MAP kinase inhibition by U0126 matures mouse proliferating hepatocytes

| GENE | VEHICLE TREATED MOUSE ADULT PROLIFERATING HEPATOCYTES | U0126 TREATED MOUSE ADULT PROLIFERATING HEPATOCYTES |
| --- | --- | --- |
| CYP3A11 (human adult CYP3A4) | 496 | 563 |
| CYP3A16 (human fetal CYP3A4) | 15 | 2 |
| UGT1A1 | 6 | 54 |
| UGT1A6A | 28 | 189 |
| APOB | 332 | 567 |
| APOH | 128 | 245 |
| HNF4A | 254 | 340 |
| AHR | 4 | 11 |
| RARA | 1 | 5 |
| RXRA | 28 | 40 |

Figure 6:
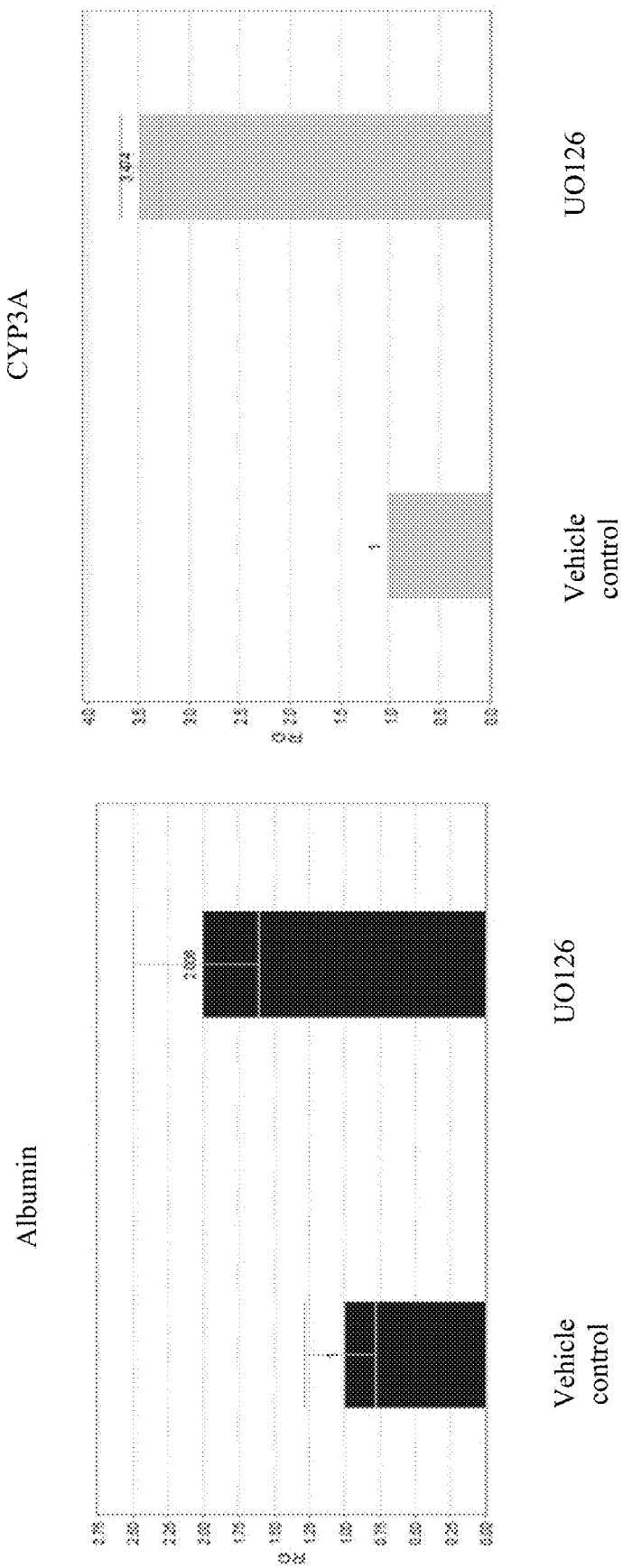
FIG. 6 shows U0126 treatment of ESC-hepatocyte derived SHPCs produces mature hepatocytes as evidenced by increase in the RQ of albumin (left) and CYP3A (right).
Figure 7:
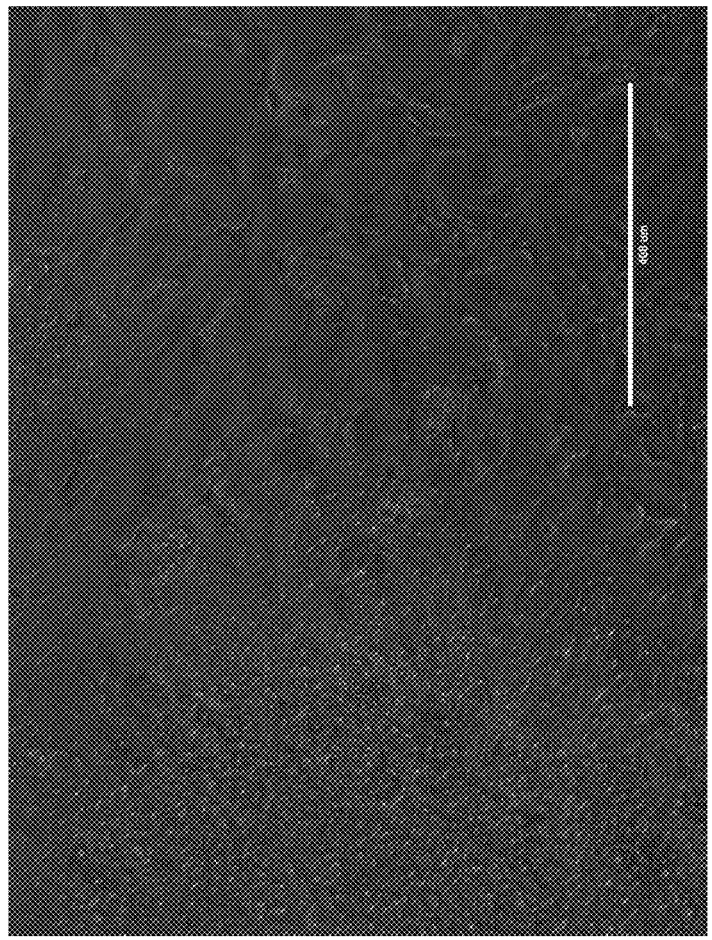
FIG. 7 shows SHPCs derived from Hu1962 hepatocytes cultured on MATRIGEL™. Cells in the middle show good hepatocyte morphology (small with clear nuclei) and the cells on the edges are de-differentiated with morphology that is visibly bigger and flatter than mature adult hepatocytes.
Figure 8:
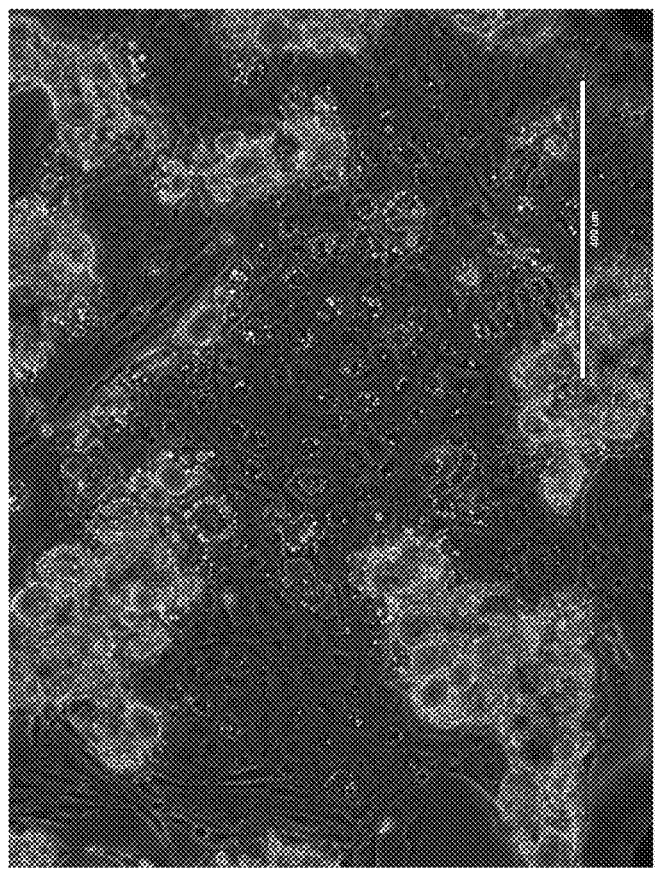
FIG. 8 shows growth of primary human hepatocytes (PHH) in the YAC medium described by Katsuda et al. (Katsuda et al., Cell Stem Cell, 2017). The YAC medium of Katsuda does not support human hepatocyte culture. While YAC treatment gave rise to a few colonies of hepatocytes (one such colony pictured on the left), they rapidly dedifferentiated (pictured on right) and died off.
Figure 8:
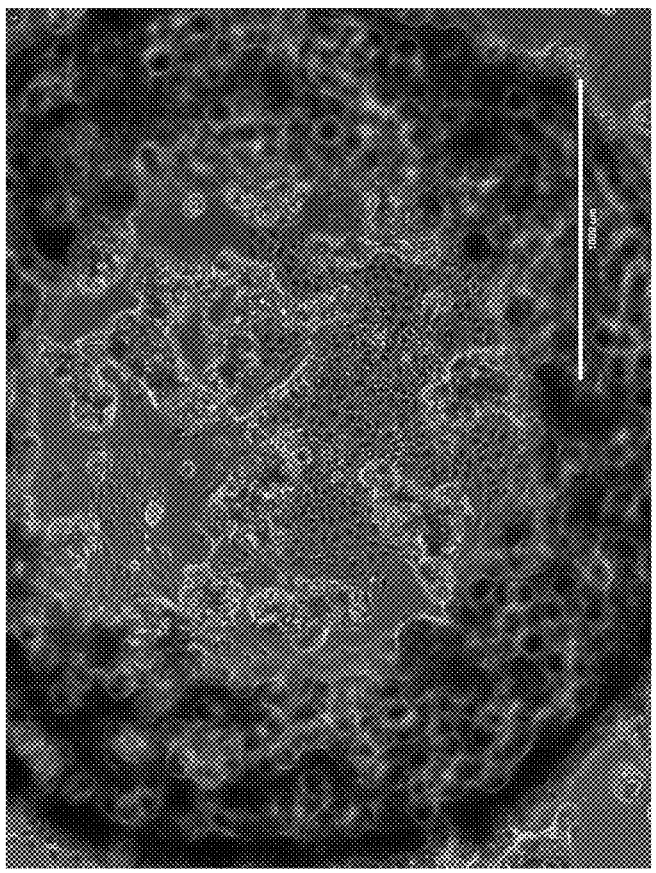
Figure 9:
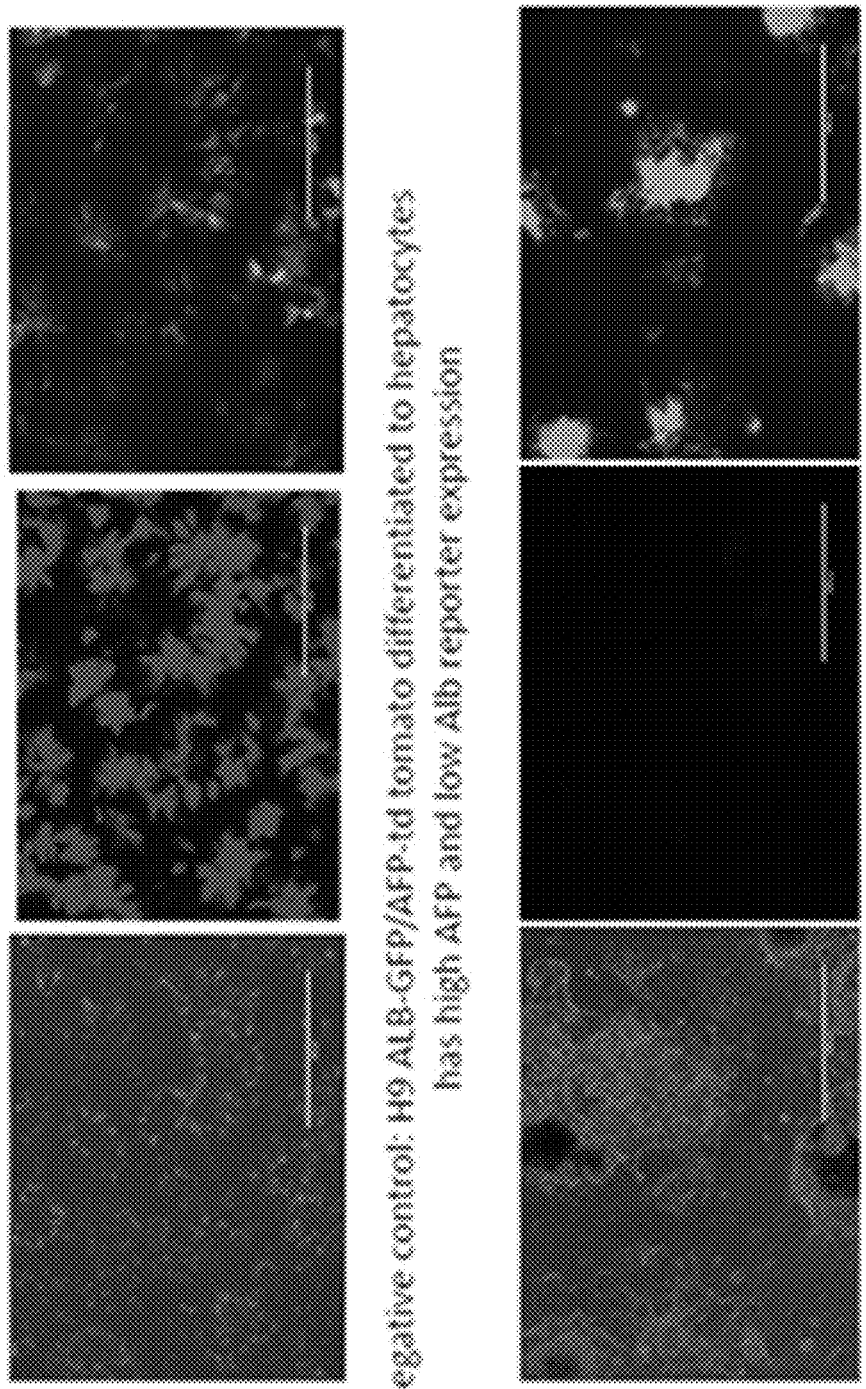
FIG. 9 shows SHPC derivation matures ESC-hepatocytes. Top: negative control showing duel reporter (expressing GFP and TdTomato from albumin and alpha feto-protein (AFP) respectively) H9 clone ESC-hepatocytes have high AFP and low albumin reporter expression. Bottom: SHPCs derived from ESC-hepatocytes display more maturity, with high albumin and low AFP reporter expression.
Figure 10:
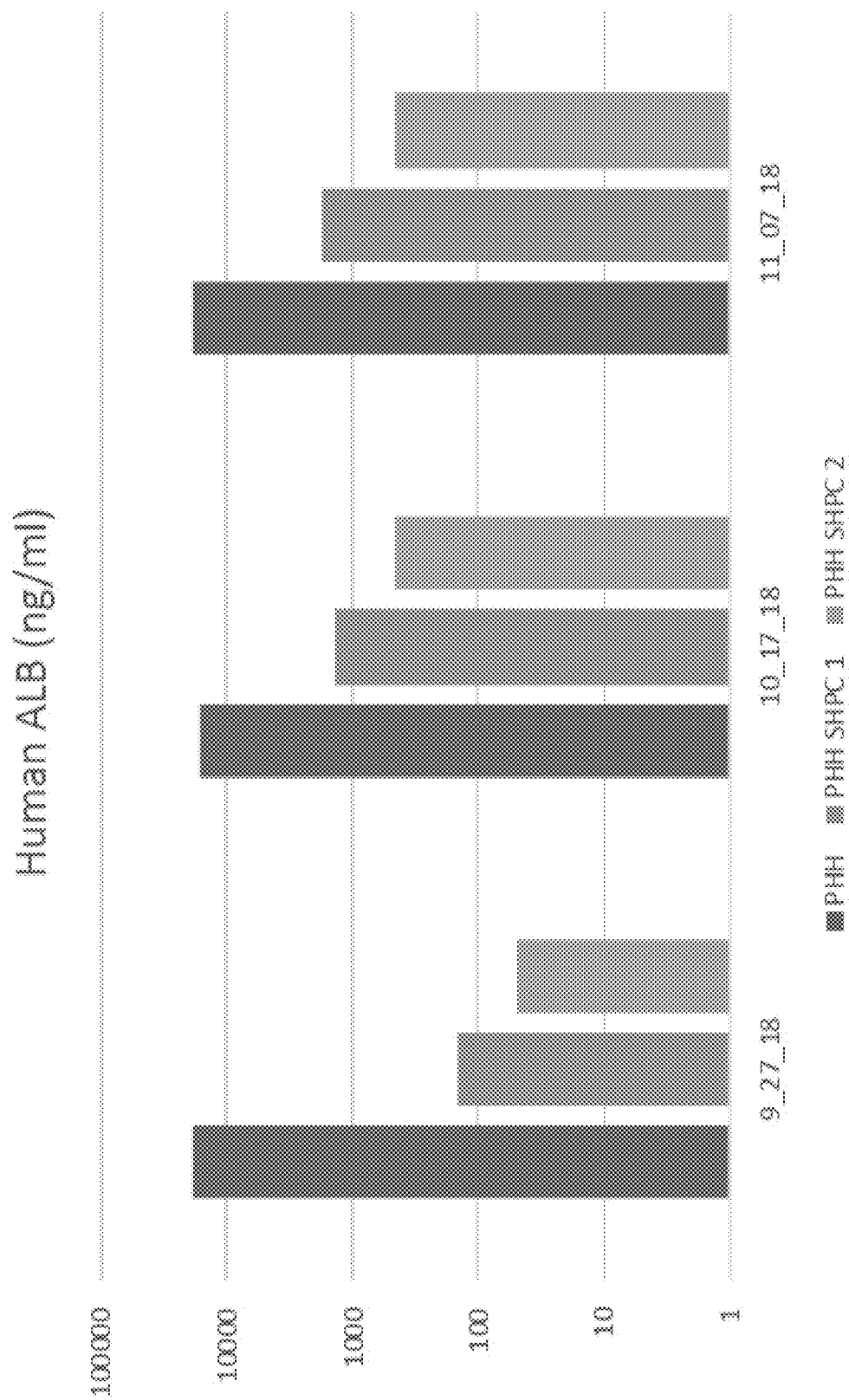
FIG. 10 shows PHH derived SHPCs engraft in Tk-NOG mice. PHH-SHPC transplanted mice show human albumin in their blood at levels close to the levels in control PHH transplanted mice.
Figure 11:
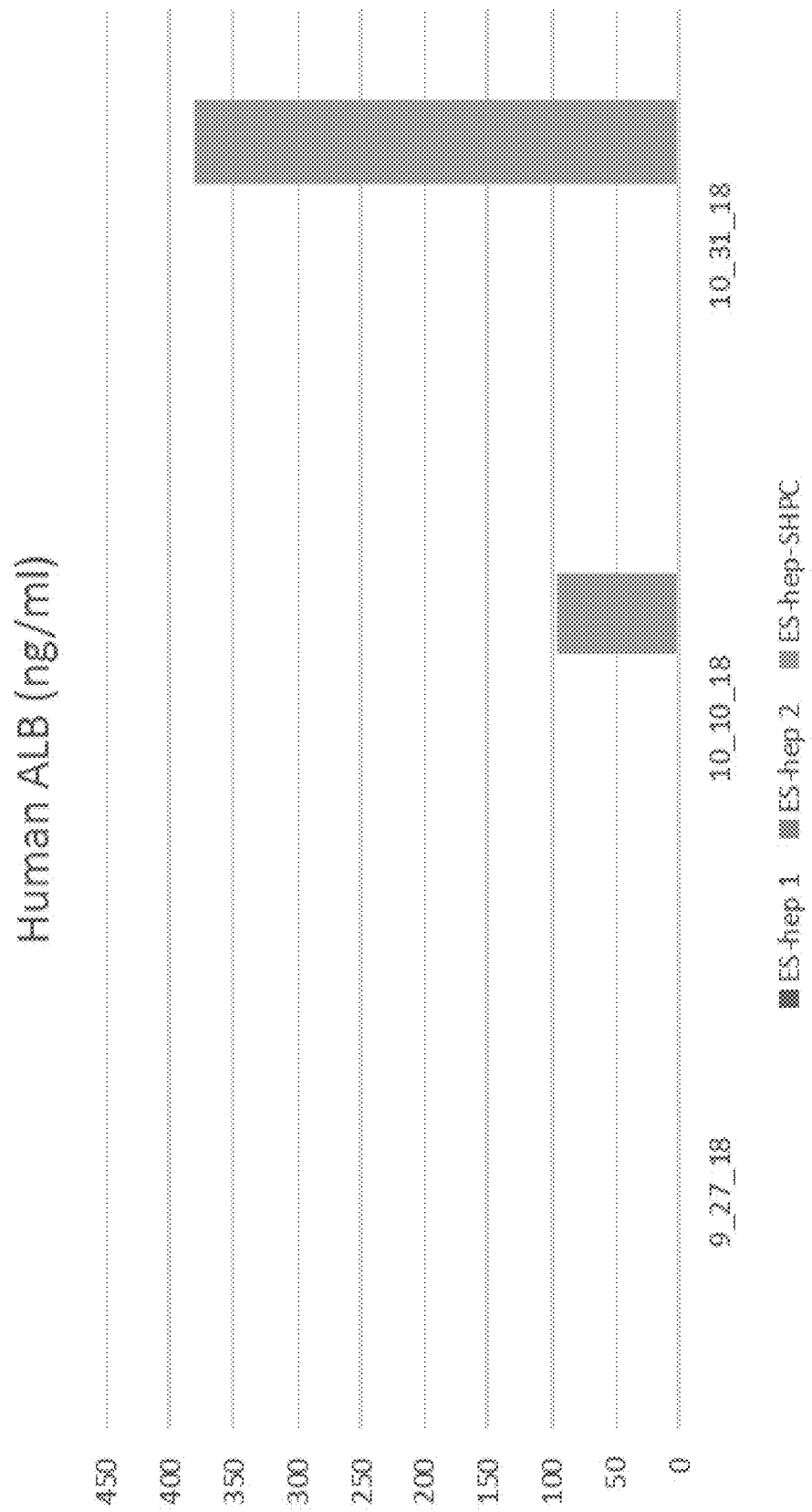
FIG. 11 shows ESC-hepatocyte derived SHPCs engraft in Tk-NOG mice. ESC-hepatocyte transplanted mice do not show human albumin in blood, but ESC-hepatocyte derived SHPCs do show human albumin in blood, which increases over time to levels comparable to PHH-SHPC transplanted mice.
Figure 12:
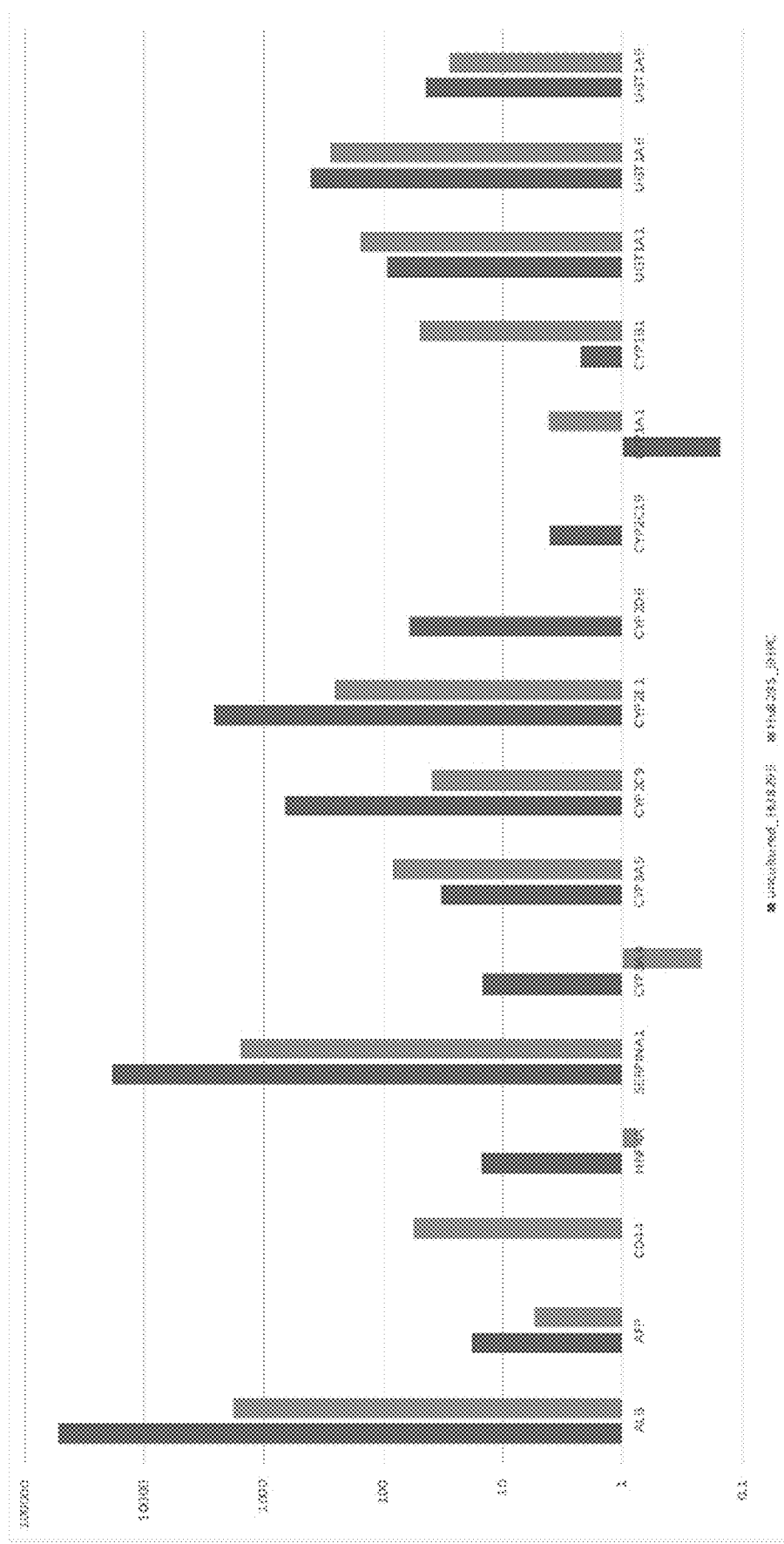
FIG. 12 shows expression of phase I and phase II gene in PHH SHPCs from donor HU8295, a 19-year-old male.
Figure 13:
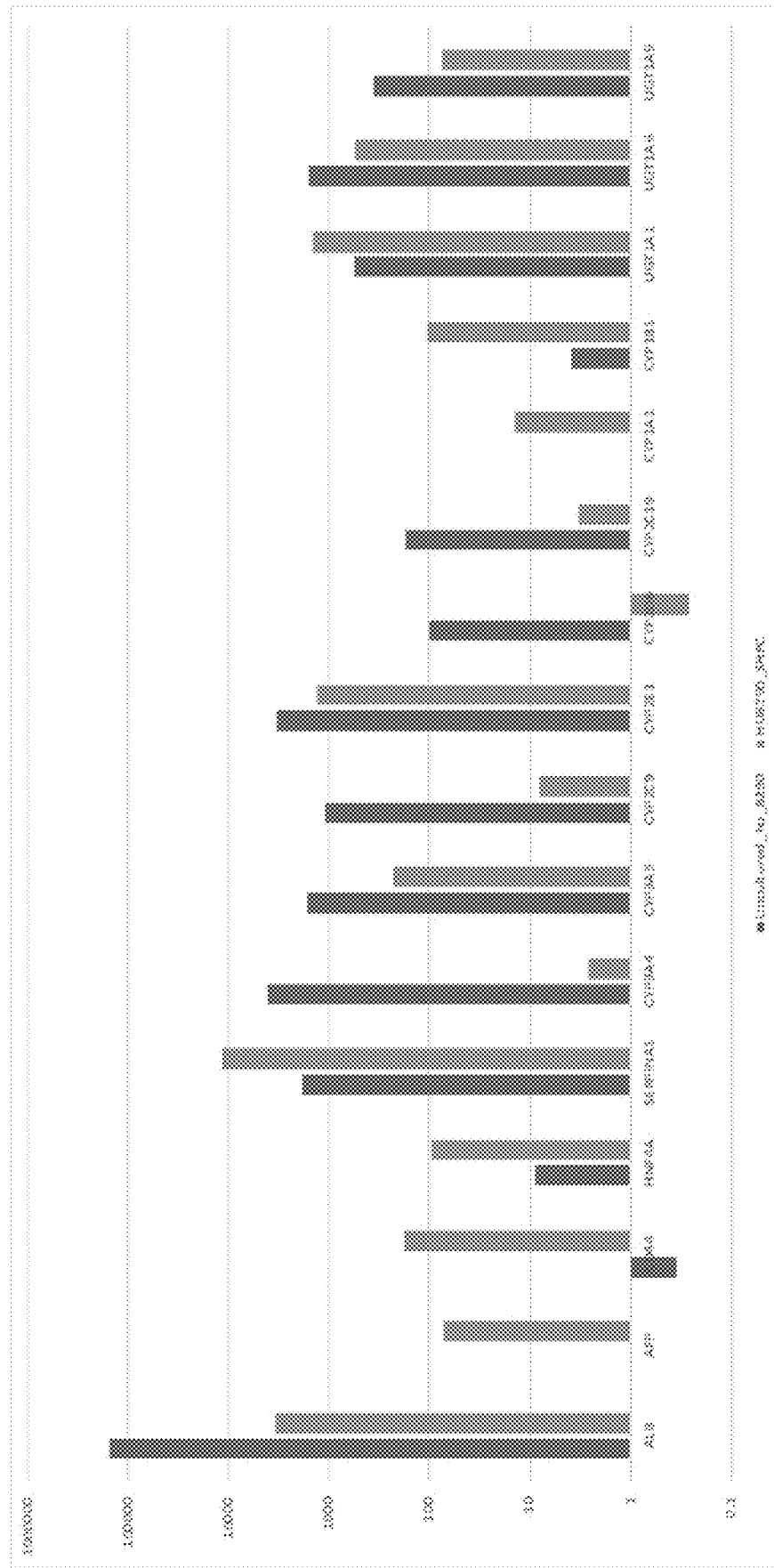
FIG. 13 shows expression of phase I and phase II gene in PHH SHPCs from donor HU8290, a 23-year-old female.
Figure 14:
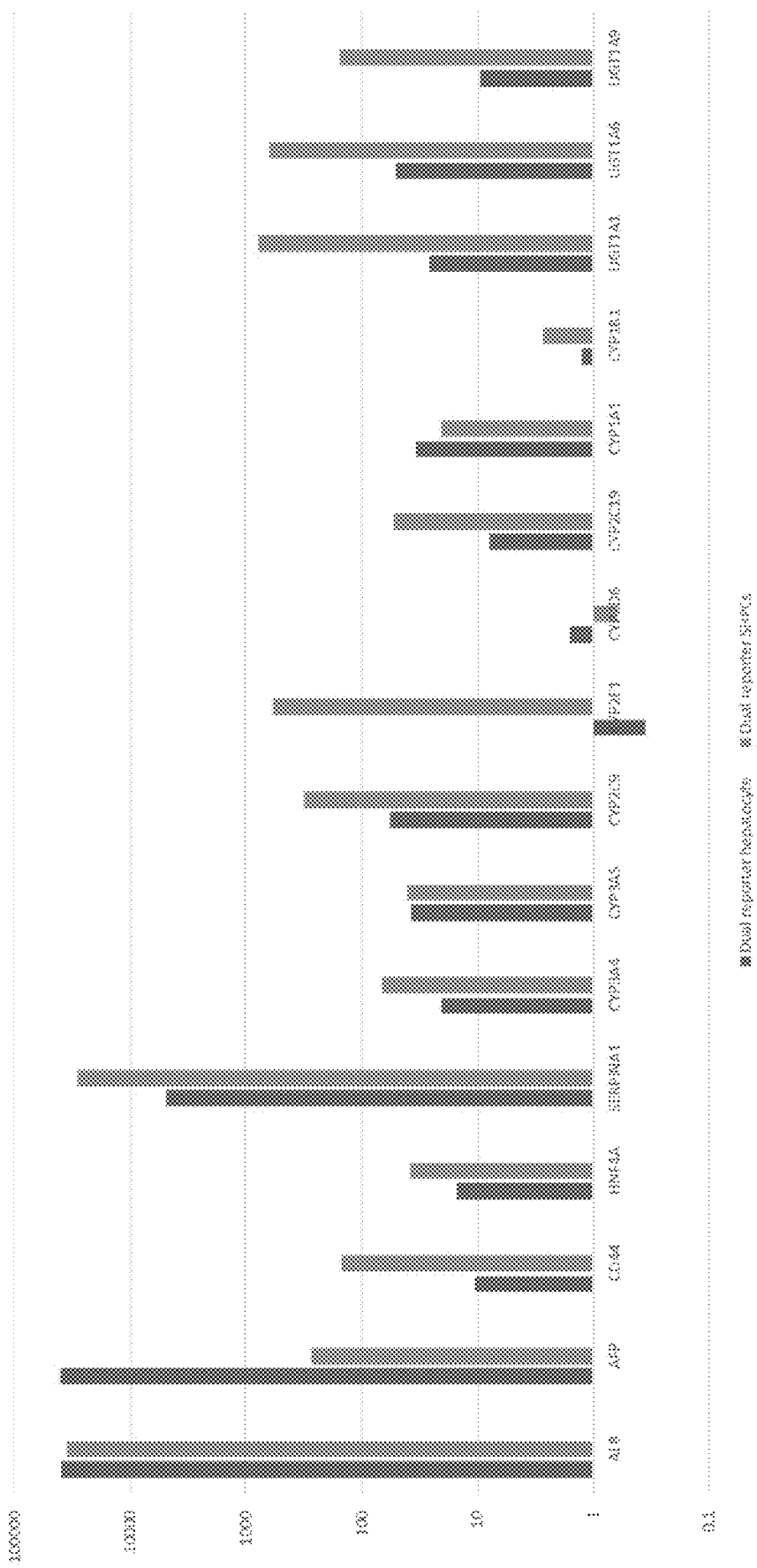
FIG. 14 shows expression of phase I and phase II gene in ESC-hepatocyte derived SHPCs.
Figure 15:
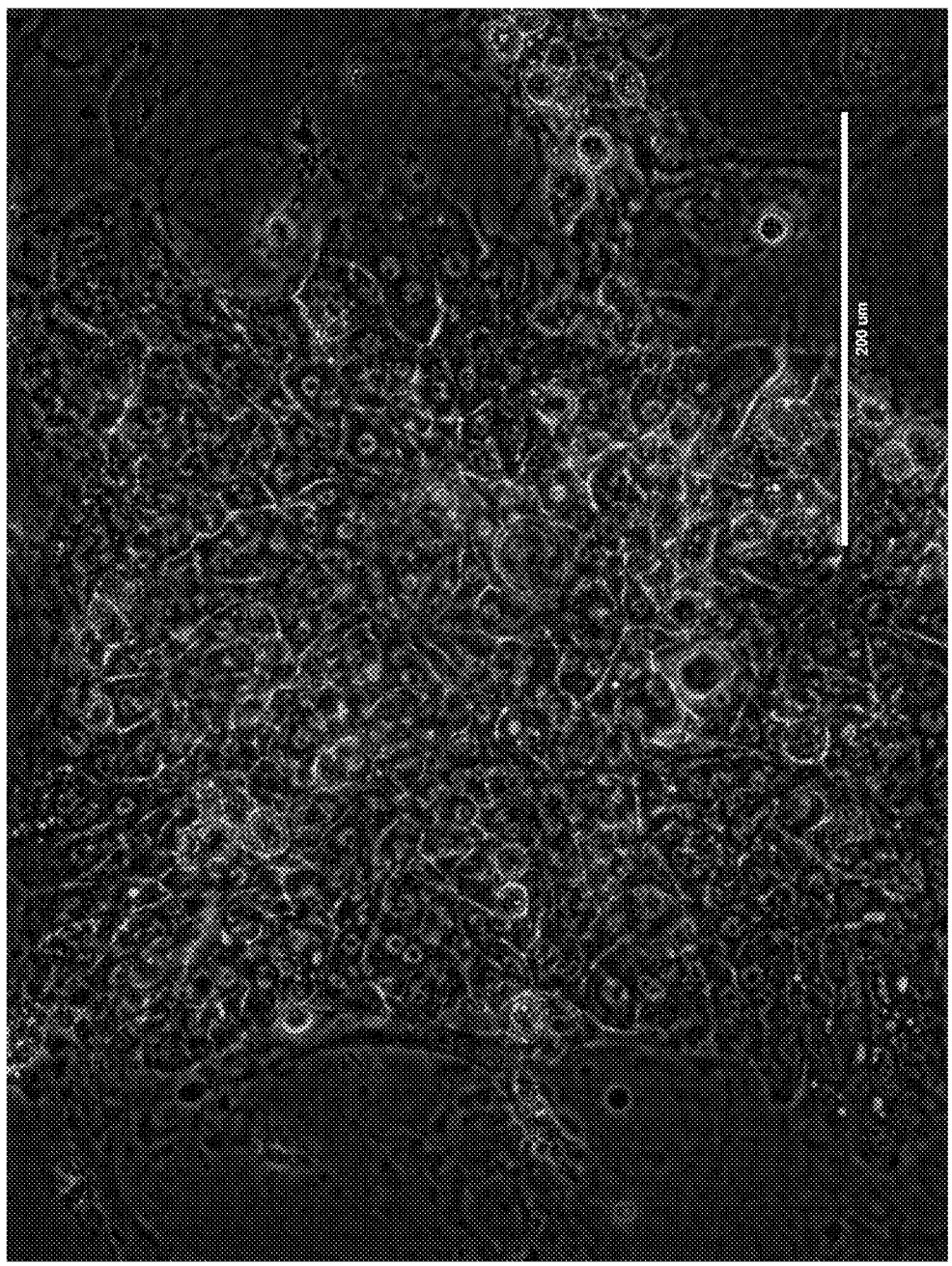
FIG. 15 shows HU8290 SHPCs.

We treated the ESC-hepatocyte derived SHPCs in SHPC medium and co-cultured with MEFs and U0126. We FAC sorted the albumin reporter expressing hepatocytes and performed QPCR. FIG. 6 shows a 2-fold increase in albumin expression and a 3-fold increase in CYP3A expression in cells cultured with U0126, confirming their maturation. Table 1 shows RNA-seq data from SHPCs derived from ES-hepatocytes.

SHPC Metabolic Activity—

Figure 16:
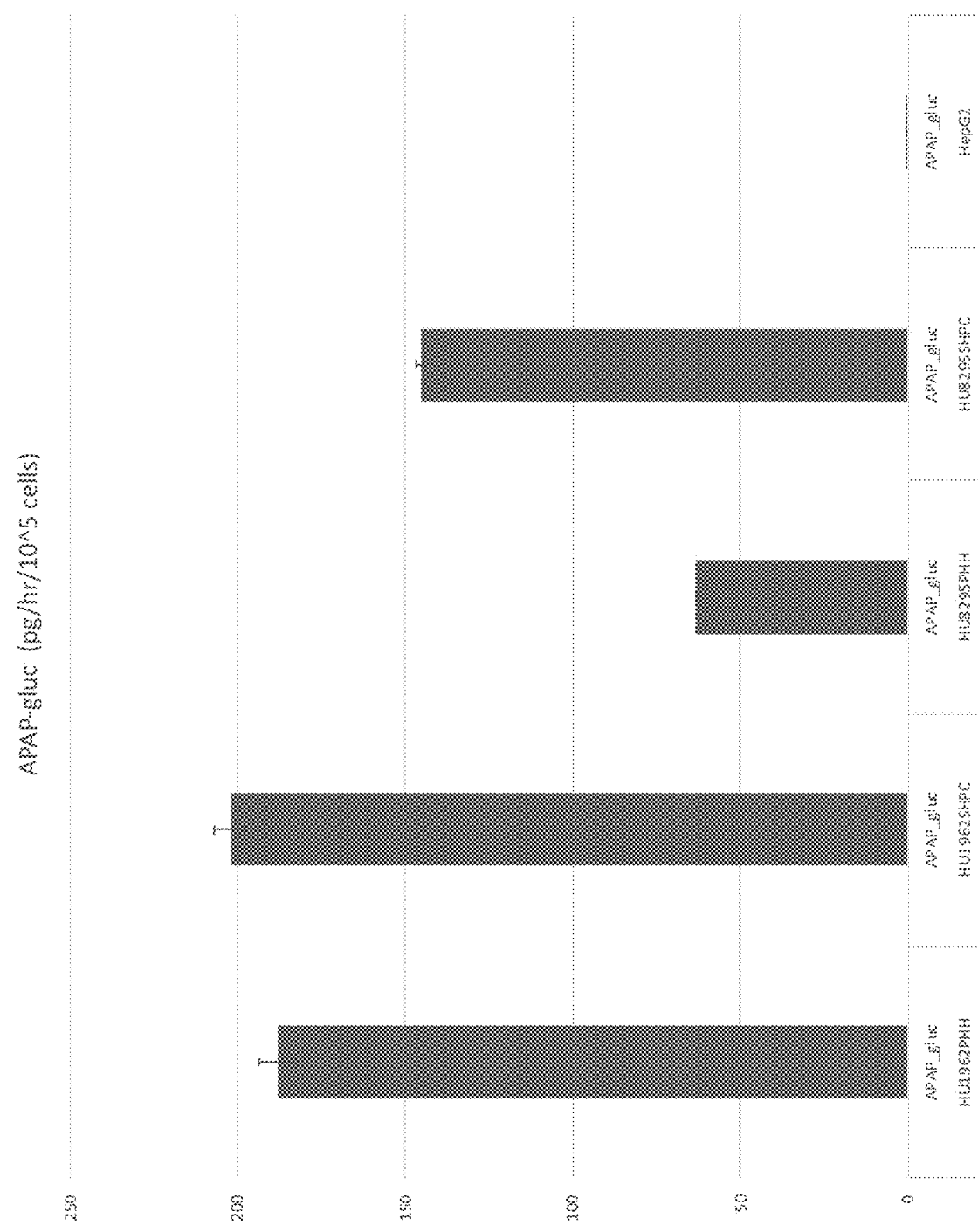
FIG. 16 shows acetaminophen glucuronide (APAP-gluc) production in HU1962 PHH, HU1962 SHPCs, HU8295 PHH, and HU8295 SHPCs, and control HepG2 cells. APAP-gluc production is measured in pg per hour per $10^5$ cells.
Figure 17:
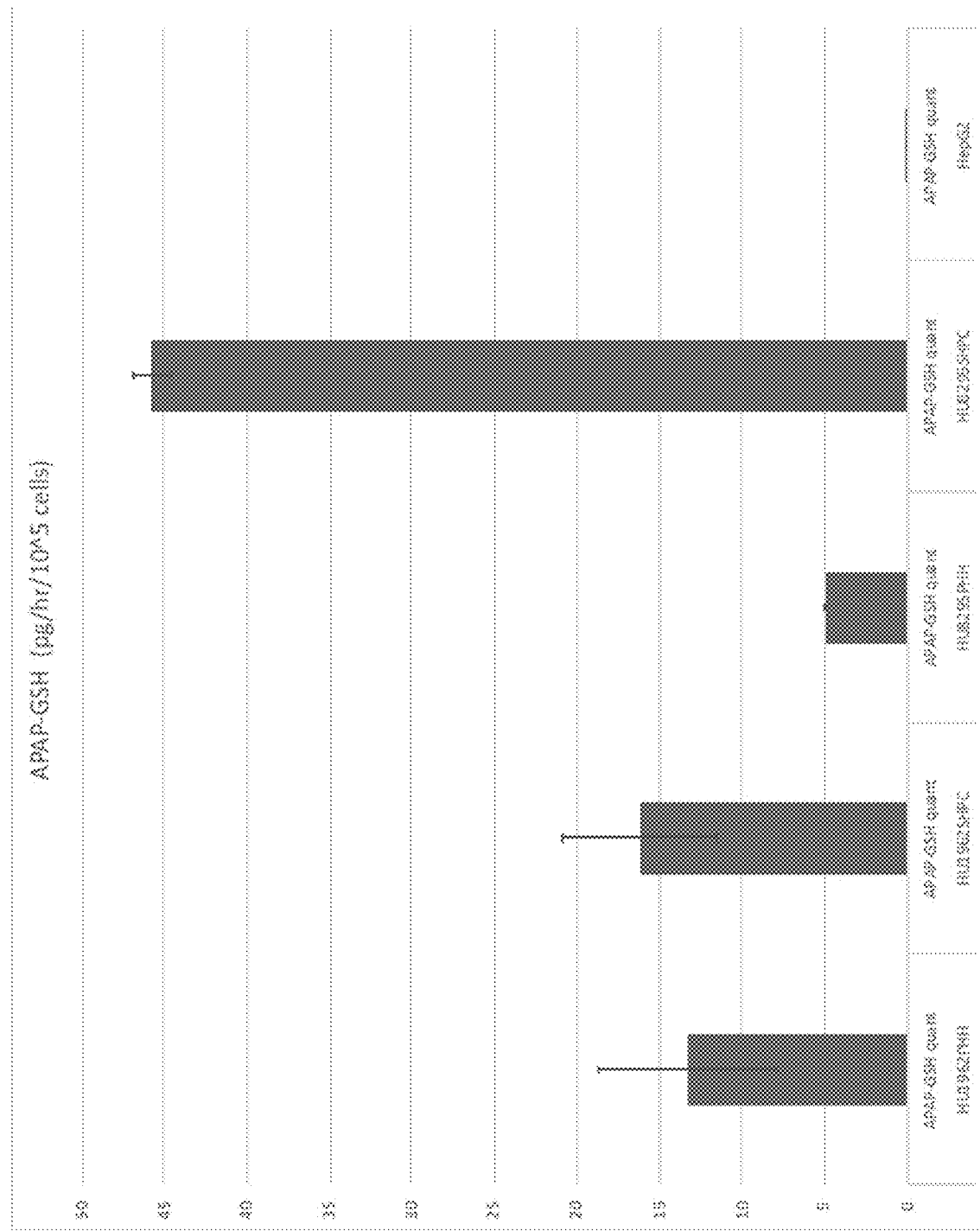
FIG. 17 shows acetaminophen glutathione (APAP-GSH) production in HU1962 PHH, HU1962 SHPCs, HU8295 PHH, and HU8295 SHPCs, and control HepG2 cells. APAP-GSH production is measured in pg per hour per $10^5$ cells.
Figure 18:
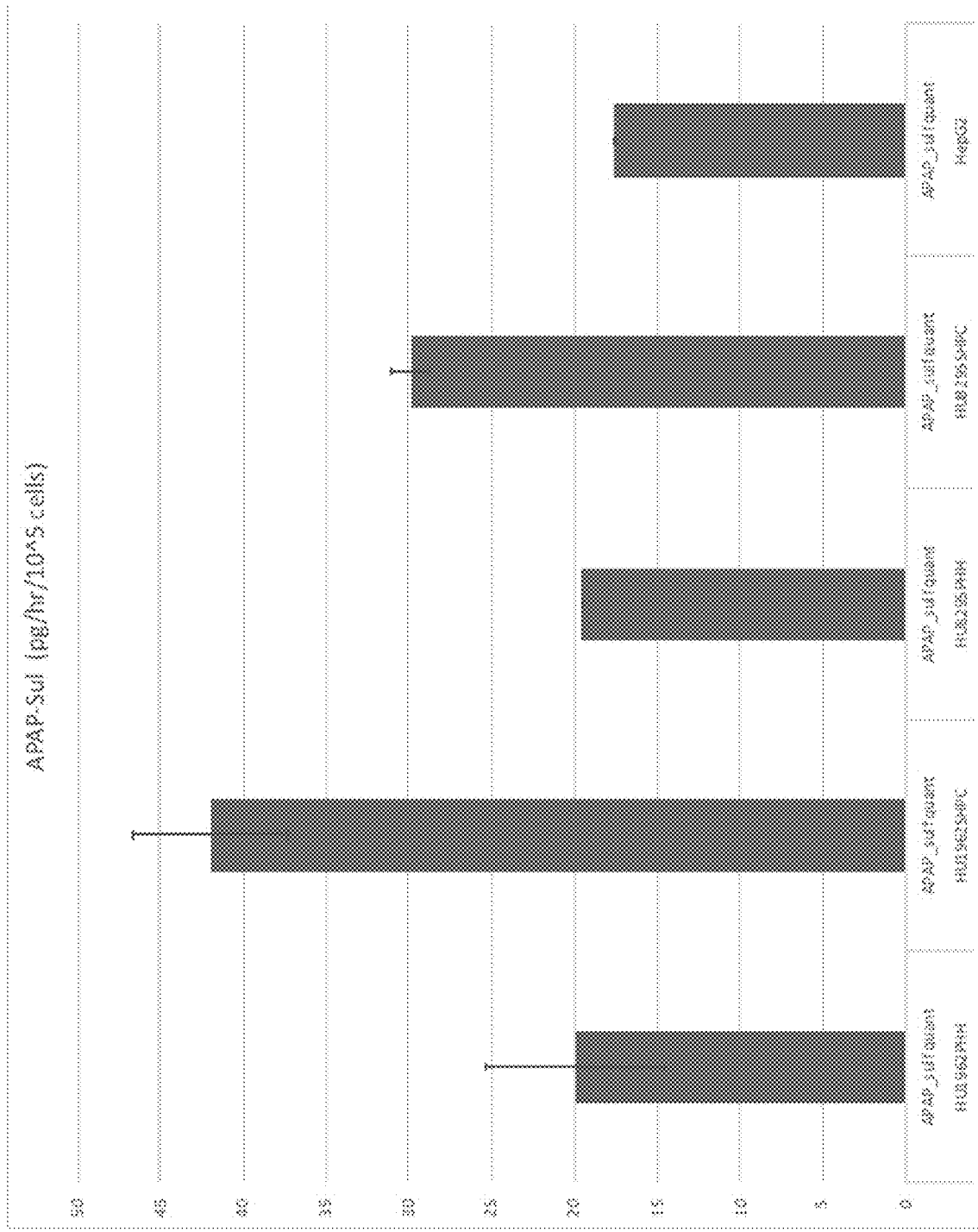
FIG. 18 shows acetaminophen sulfate (APAP-Sul) production in HU1962 PHH, HU1962 SHPCs, HU8295 PHH, and HU8295 SHPCs, and control HepG2 cells. APAP-Sul production is measured in pg per hour per $10^5$ cells.

FIGS. 16 and 18 show that SHPCs breakdown acetaminophen to APAP-gluc and APAP-sul, which are products of the phase II metabolic pathway. APAP-GSH (FIG. 17) is a product of both phase I and phase II metabolic pathways. This data demonstrate that the SHPCs have equivalent or higher metabolic activity to the starting population of primary human hepatocytes from which the SHPCs were differentiated. Metabolic activity was assayed after the SHPCs has been through 3 passages, demonstrating that these cells are stable and proliferating in culture and maintain their metabolic activity long term.

DISCUSSION

We here show the derivation, culture and maturation of SHPCs from adult human liver derived hepatocytes. These cells will be useful in multiple ways; they will close the huge difference between demand and supply that exists in the pharmaceutical industry for hepatocytes needed for drug development and drug metabolism studies/metabolite identification, toxicity testing and drug-drug interaction studies. They will also be useful for development of drugs against hepatotropic viruses that cause cirrhosis and liver cancer as well as other inherited and acquired liver diseases. These cells can be used to humanize mouse livers for studying the role of immune system in development of chronic inflammation in the liver and establishment of viral infection both of which lead to cirrhosis and liver cancer. These cells can be used for transplantation in the clinic for regeneration of diseased livers. Finally, they can be potentially used for fabrication of extracorporeal liver assist devices and bioartificial livers.

REFERENCES

Mitaka T, Sato F, Mizuguchi T, Yokono T, Mochizuki Y. (1999). Reconstruction of hepatic organoid by rat small hepatocytes and hepatic nonparenchymal cells. Hepatology. 29(1): 111-25.

Gordon G J, Butz G M, Grisham J W, Coleman W B. (2002). Isolation, short-term culture, and transplantation of small hepatocyte-like progenitor cells from retrorsine-exposed rats. Transplantation. 73(8): 1236-43.

Avril A, Pichard V, Bralet M P, Ferry N. (2004). Mature hepatocytes are the source of small hepatocyte-like progenitor cells in the retrorsine model of liver injury. J Hepatol. 41(5):737-43.

Best D H, Coleman W B. (2010). Liver regeneration by small hepatocyte-like progenitor cells after necrotic injury by carbon tetrachloride in retrorsine-exposed rats. Exp Mol Pathol. 89(2): 92-8.

Katsuda T, Kawamata M, Hagiwara K, Takahashi R U, Yamamoto Y, Camargo F D, Ochiya T. (2017). Conversion of Terminally Committed Hepatocytes to Culturable Bipotent Progenitor Cells with Regenerative Capacity. Cell Stem Cell. 20(1): 41-55.

Ping C, Xiaoling D, Jin Z, Jiahong D, Jiming D, Lin Z. (2006). Hepatic sinusoidal endothelial cells promote hepatocyte proliferation early after partial hepatectomy in rats. Arch Med Res. 37(5): 576-83.

Chen G, Gulbranson D R, Hou Z, Bolin J M, Ruotti V, Probasco M D, Smuga-Otto K, Howden S E, Diol N R, Propson N E, Wagner R, Lee G O, Antosiewicz-Bourget J, Teng J M, Thomson J A. (2011). Chemically defined conditions for human iPSC derivation and culture. Nat Methods. 8(5): 424-9.

We claim:

1. A method for obtaining CD44+ small hepatocyte progenitor cells, the method comprising: culturing human hepatocytes in the presence of embryonic fibroblasts in a culture medium that comprises Y27632, A-83 01, and CHIR99021, epidermal growth factor, N2, and B27, whereby a cell population comprising CD44+ small hepatocyte progenitor cells is obtained.

2. The method of claim 1, wherein the culture medium further comprises dexamethasone.

3. The method of claim 2, wherein the culture medium further comprises Oncostatin M, fetal bovine serum, and nicotinamide.

4. The method of claim 1, wherein the human hepatocytes are selected from the group consisting of primary human hepatocytes and pluripotent stem cell-derived human hepatocytes.

5. The method of claim 4, wherein the pluripotent stem cell-derived hepatocytes are selected from the group consisting of embryonic stem cell-derived hepatocytes or induced pluripotent stem cell-derived hepatocytes.

6. The method of claim 1, wherein the embryonic fibroblasts are mouse embryonic fibroblasts or human embryonic fibroblasts.

7. The method of claim 1, wherein the human hepatocytes are cultured for about 6 days to obtain a cell population comprising CD44+ small hepatocyte progenitor cells.

* * * * *